US010107822B2

(12) United States Patent
Marr

(10) Patent No.: US 10,107,822 B2
(45) Date of Patent: Oct. 23, 2018

(54) INTERFERON-GAMMA RELEASE ASSAYS FOR DIAGNOSIS OF INVASIVE FUNGAL INFECTIONS

(71) Applicant: THE JOHNS HOPKINS UNIVERSITY, Baltimore, MD (US)

(72) Inventor: Kieren Marr, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 3 days.

(21) Appl. No.: 15/105,179

(22) PCT Filed: Dec. 16, 2014

(86) PCT No.: PCT/US2014/070610
§ 371 (c)(1),
(2) Date: Jun. 16, 2016

(87) PCT Pub. No.: WO2015/095195
PCT Pub. Date: Jun. 25, 2015

(65) Prior Publication Data
US 2016/0313346 A1 Oct. 27, 2016

Related U.S. Application Data

(60) Provisional application No. 61/916,542, filed on Dec. 16, 2013, provisional application No. 62/062,523, filed on Oct. 10, 2014.

(51) Int. Cl.
G01N 33/68 (2006.01)
G01N 33/53 (2006.01)
C07K 14/57 (2006.01)

(52) U.S. Cl.
CPC ......... *G01N 33/6866* (2013.01); *C07K 14/57* (2013.01); *G01N 2333/37* (2013.01); *G01N 2333/39* (2013.01); *G01N 2333/57* (2013.01); *G01N 2800/26* (2013.01)

(58) Field of Classification Search
None
See application file for complete search history.

(56) References Cited

U.S. PATENT DOCUMENTS

| 4,943,522 | A | 7/1990 | Eisinger et al. |
| 5,149,632 | A | 9/1992 | Notermans et al. |
| 5,710,005 | A | 1/1998 | Rittenburg |
| 5,766,961 | A | 6/1998 | Pawlak et al. |
| 5,876,961 | A | 3/1999 | Crowe et al. |
| 5,945,294 | A | 8/1999 | Frank et al. |
| 6,500,629 | B1 | 12/2002 | Cleaver et al. |
| 7,097,983 | B2 | 8/2006 | Markovsky et al. |
| 7,371,582 | B2 | 5/2008 | Nahm et al. |
| 9,274,111 | B2 * | 3/2016 | Luppi ............ G01N 33/56961 |
| 9,915,657 | B2 * | 3/2018 | Marr ............ G01N 33/56961 |
| 2002/0045195 | A1 | 4/2002 | Hubscher et al. |
| 2003/0082533 | A1 | 5/2003 | Yue et al. |
| 2003/0148484 | A1 | 8/2003 | Koentgen et al. |
| 2004/0018556 | A1 | 1/2004 | Cantor |
| 2005/0042738 | A1 | 2/2005 | Swarnaker et al. |
| 2005/0074410 | A1 | 4/2005 | Reto Cramer et al. |
| 2005/0214836 | A1 | 9/2005 | Nakamura et al. |
| 2005/0214951 | A1 | 9/2005 | Nahm et al. |
| 2005/0272106 | A1 | 12/2005 | Moore et al. |
| 2006/0019406 | A1 | 1/2006 | Wei et al. |
| 2006/0121626 | A1 | 6/2006 | Imrich |
| 2006/0127886 | A1 | 6/2006 | Kaylor et al. |
| 2006/0134608 | A1 | 6/2006 | Guo et al. |
| 2006/0148102 | A1 | 7/2006 | Guo et al. |
| 2006/0241288 | A1 | 10/2006 | Roche et al. |
| 2007/0020711 | A1 | 1/2007 | Wheat |
| 2008/0147031 | A1 | 6/2008 | Long et al. |
| 2009/0117585 | A1 | 5/2009 | Van Den Hondel |
| 2010/0119533 | A1 | 5/2010 | Clancy et al. |
| 2010/0168023 | A1 | 7/2010 | Ruegg et al. |
| 2012/0064093 | A1 | 3/2012 | Thornton |
| 2013/0017561 | A1 * | 1/2013 | Marr ............ G01N 33/569 435/7.92 |
| 2013/0130274 | A1 | 5/2013 | Kelly |
| 2013/0260395 | A1 * | 10/2013 | Luppi ............ G01N 33/56961 435/7.24 |
| 2014/0178884 | A1 | 6/2014 | Aucoin et al. |
| 2014/0212436 | A1 | 7/2014 | Moore et al. |
| 2016/0313346 | A1 * | 10/2016 | Marr ............ G01N 33/6866 |

FOREIGN PATENT DOCUMENTS

| EP | 0325004 A1 | 7/1989 |
| EP | 1104768 A1 | 6/2001 |
| EP | 1430902 A1 | 6/2004 |
| WO | 2007011221 A2 | 1/2007 |

(Continued)

OTHER PUBLICATIONS

Barnes et al, Risks, diagnosis and outcomes of invasive fungal infections in haematopoietic stem cell transplant recipients. British Journal of Haematology, 2007, 139/4:519-531 (Year: 2007).*
El-Muzghi et al, Regional cytokine responses to pulmonary aspergillosis in immunocompetent rats, Jun. 7, 2013, Immunobiology, 218:1514-1523 (Year: 2013).*
Hagl et al, Key findings to expedite the diagnosis of hyper-IgE syndromes in infants and young children, Pediatric Allergy and Immunology 27 (2016) 177-184 (Year: 2016).*
Marr et al, Detection of Galactomannan Antigenemia by Enzyme Immunoassay for the Diagnosis of Invasive Aspergillosis: Variables That Affect Performance, Journal of Infectious Diseases, Aug. 1, 2004, 190/3:641-649 (Year: 2004).*

(Continued)

Primary Examiner — Nita M. Minnifield
(74) Attorney, Agent, or Firm — Casimir Jones, S.C.; Jeffrey W. Childers

(57) ABSTRACT

Methods, kits, and diagnostic devices are disclosed for diagnosing an invasive fungal infection in a subject by measuring a T-cell interferon gamma (IFN-γ) response after exposure to a fungal antigen.

23 Claims, 13 Drawing Sheets

(56) References Cited

FOREIGN PATENT DOCUMENTS

| WO | 2007015177 A2 | 2/2007 | |
|---|---|---|---|
| WO | WO-2015095195 A1 * | 6/2015 | ......... G01N 33/6866 |

OTHER PUBLICATIONS

Shen et al, Efficiency of interleukin 6 and interferon gamma in the differentiation of invasive pulmonary aspergillosis and pneumocystis pneumonia in pediatric oncology patients, International Journal of Infectious Diseases, 2016, 48:73-77 (Year: 2016).*

Tongchusak et al, Promiscuous T cell epitope prediction of Candida albicans secretory aspartyl protienase family of proteins, Infection, genetics and Evolution, 2008, 8:467-473 (Year: 2008).*

Thornton, "Development of an immunochromatographic lateral—flow device for rapid serodiagnosis of invasive aspergillosis." Clin Vaccine Immunol, Jul. 2008;15(7): p. 1095-105.

Upton et al., "(1>3) beta-D-glucan assay in the diagnosis of invasive fungal infections." Clin Infect Dis, 2006. 42(7): p. 1054-6; author reply 1056.

Wald et al., "Epidemiology of Aspergillus infections in a large cohort of patients undergoing bone marrow transplantation." The Journal of Infectious Diseases, 1997. 175: p. 1459-66.

Walsh et al., "Experimental pulmonary aspergillosis due to Aspergillus terreus: pathogenesis and treatment of an emerging fungal pathogen resistant to amphotericin B." J Infect Dis, 2003. 188(2): p. 305-19.

Wood, K. L., C. A. Hage, K. S. Knox, M. B. Kleiman, A. Sannuti, R. B. Day, L. J. Wheat, and H. L. Twigg, 3rd. 2003. Histoplasmosis after treatment with anti-tumor necrosis factor-alpha therapy. Am. J. Respir. Crit Care Med. 167:1279-1282.

Hebart et al., "Early detection of aspergillus infection after allogeneic stem cell transplantation polymerase chain reaction screening." J Infect Dis, 2000. 181(5): p. 1713-9.

Herrera et al., "Clinical application and limitations of interferon-gamma release assays for the diagnosis of latent tuberculosis infection," Clinical Infectious Diseases, vol. 52, No. 8, pp.

Hohl et al., "Aspergillus fumigatus triggers inflammatory responses by stage-specific beta-glucan display." PLoS Pathog, 2005. 1(3): p. e30.

Huber, F., M. Nacher, C. Aznar, M. Pierre-Demar, M. El Guedj, T. Vaz, V. Vantilcke, A. Mahamat, C. Magnien, E Chauvet, B. Carme, and P. Couppie. 2008. AIDS—related Histoplasma capsulatum var. capsulatum infection: 25 years experience of French Guiana. Aids 22:1047-1053.

Hurst et al., "Comparison of Commercial Latex Agglutination and Sandwich Enzyme Immunoassays with a Competitive Binding Inhibition Enzyme Immunoassay for Detection of Antigenemia and Antigenuria in a Rabbit Model of Invasive Aspergillosis," Clin. Diag. Lab. Immun., vol. 7, No. 3, May 2000, pp. 477-485.

Husain et al., "Aspergillus galactomannan antigen in the bronchoalveolar lavage fluid for the diagnosis of invasive aspergillosis in lung transplant recipients." Transplantation, 2007. 83(10): p. 1330-6.

Husain et al., "Performance characteristics of the platelia Aspergillus enzyme immunoassay for detection of Aspergillus galactomannan antigen in bronchoalveolar lavage fluid." Clin Vaccine Immunol, 2008. 15(12): p. 1760-3.

Inglis, D. O., M. Voorhies, D. R. Hocking Murray, and A. Sil. 2013. Comparative transcriptomics of infectious spores from the fungal pathogen Histoplasma capsulatum reveals a core set of transcripts that specify infectious and pathogenic states. Eukaryot. Cell 12:828-852.

Israel et al., "Sarcoidosis and aspergilloma: The role of surgery" Chest, 1982. 82: p. 430-432.

Kami et al., "Use of real-time PCR on blood samples for diagnosis of invasive aspergillosis." Clin Infect Dis, 2001. 33 (9): p. 1504-12.

Kappe et al., "New cause for false-positive results with the Pastorex Aspergillus antigen latex agglutination test." J Clin Microbial, 1993. 31(9): p. 2489-90.

Kawamura et al., "Clinical evaluation of 61 patients with pulmonary aspergilloma." Intern Med, 2000. 39(3): p. 209-12.

Khot et al., "Development and optimization of quantitative PCR for the diagnosis of invasive aspergillosis with bronchoalveolar lavage fluid." BMC Infect Dis, 2008. 8: p. 73.

Klont et al., "Utility of Aspergillus antigen detection in specimens other than serum specimens." Clin Infect Dis, 2004. 39(10): p. 1467-74.

Koide et al., "Comparative evaluation of Duopath Legionella lateral flow assay against the conventional culture method using Legionella pneumophila and Legionella anisa strains." Jpn J Infect Dis, 2007. 60(4): p. 214-6.

Kroetz, D. N., and G. S. Deepe. 2012. The role of cytokines and chemokines in Histoplasma capsulatum infection. Cytokine 58:112-117.

Latge, Jean-Paul et al, Infection and Immunity, vol. 62(12), Dec. 1994, pp. 5424-5433, "Chemical and Immunological Characterization of the Extracellular Galactomannan of Aspergillus fumigatus".

Maertens et al., "Optimization of the cutoff value for the Aspergillus double-sandwich enzyme immunoassay." Clin Infect Dis, 2007. 44(10): p. 1329-36.

Marr et al., "Epidemiology and outcome of mould infections in hematopoietic stem cell transplant recipients." Clin Infect Dis, 2002. 34: p. 909-917.

Marr et al., "Detection of galactomannan antigenemia by enzyme immunoassay for the diagnosis of invasive aspergillosis: variables that affect performance." J Infect Dis, 2004. 190(3): p. 641-9.

Marr et al., "Design issues in studies evaluating diagnostic tests for aspergillosis." Clin Infect Dis, 2005.41 Suppl 6: p. S381-6.

Marr, "Aspergillus galactomannan index: a surrogate end point to assess outcome of therapy?" Clin Infect Dis, 2008. 46(9): p. 1423-5.

Meersseman et al., "Galactomannan in bronchoalveolar lavage fluid: a tool for diagnosing aspergillosis in intensive care unit patients." Am J Respir Crit Care Med, 2008. 177(1): p. 27-34.

Mennink-Kersten, M. et al., "In Vitro Release by Aspergillus fumigatus of GA lactofuranose Antigens, 1,3-beta-D-Glucan, and DNA, Surrogate Markers Used f or Diagnosis of Invasive Aspergillosis", Journal of Clinical Microbiology, May 2006, vol. 44, No. 5, pp. 1711-1718.

Musher et al., "Aspergillus galactomannan enzyme immunoassay and quantitative PCR for diagnosis of invasive aspergillosis with bronchoalveolar lavage fluid." J Clin Microbiol, 2004. 42(12): p. 5517-22.

Neofytos et al., "Epidemiology and outcome of invasive fungal infection in adult hematopoietic stem cell transplant recipients: analysis of Multicenter Prospective Antifungal Therapy (PATH) Alliance registry." Clin Infect Dis, 2009. 48(3): p. 265-73.

Nguyen et al., "Use of bronchoalveolar lavage to detect galactomannan for diagnosis of pulmonary aspergillosis among nonimmunocompromised hosts." J Clin Microbiol, 2007. 45(9): p. 2787-92.

Nishikaku et al., "Immunolocalization of IFN-gamma in the lesions of resistant and susceptible mice to Paracoccidioides brasiliensis infection," Federation of European Microbiological Societies (FEMS) Immunology & Medical Microbiology, vol. 63, No. 2, pp. 281-288 (2011).

Nosanchuk, J. D., J. N. Steenbergen, L. Shi, G. S. Deepe, Jr., and A. Casadevall. 2003. Antibodies to a cell surface histone-like protein protect against Histoplasma capsulatum. J. Clin. Invest. 112:1164-1175.

Persat et al., "Contribution of the (1>3)-beta-D-glucan assay for diagnosis of invasive fungal infections." J Clin Microbiol, 2008. 46(3): p. 1009-13.

Pickering et al., "Evaluation of a (1>3)-beta-D-glucan assay for diagnosis of invasive fungal infections." J Clin Microbiol, 2005. 43(12): p. 5957-62.

Roson et al., "Contribution of a urinary antigen assay (Binax NOW) to the early diagnosis of pneumococcal pneurnonia." Clin Infect Dis, 2004. 38(2): p. 222-6.

Sanguinetti et al., "Comparison of real-time PCR, conventional PCR, and galactomannan antigen detection by enzyme-linked immunosorbent assay using bronchoalveolar lavage fluid samples

(56) References Cited

OTHER PUBLICATIONS from hematology patients for diagnosis of invasive pulmonary aspergillosis." J Clin Microbiol, 2003. 41(8): p. 3922-5.
Scheckelhoff, M., and G. S. Deepe, Jr. 2002. The protective immune response to heat shock protein 60 of Histoplasma capsulatum is mediated by a subset of V beta 8.1/8.2+ T cells. J. Immunol. 169:5818-5826.
Scheel, C. M., B. Samayoa, A. Herrera, M. D. Lindsley, L. Benjamin, Y. Reed, J. Hart, S. Lima, B. E. Rivera, G. Raxcaco, T. Chiller, E. Arathoon, and B. L. Gomez. 2009. Development and evaluation of an enzyme-linked immunosorbent assay to detect Histoplasma capsulatum antigenuria in immunocompromised patients. Clin. Vaccine Immunol. 16:852-858.
Schmalhorst, Philipp S. et al. "Contribution of Galactofuranose to the Virulence of the Opportunistic Pathogen Aspergillus Fumigatus." Eukaryotic Cell 7.8 (2008): 1268-1277. PMC. Web. Jun. 14, 2016.
Senn et al., "1,3-Beta-D-glucan antigenemia for early diagnosis of invasive fungal infections in neutropenic patients with acute leukemia." Clin Infect Dis, 2008. 46(6): p. 878-85.
Sheppard et al., "Comparison of three methodologies for the determination of pulmonary fungal burden in experimental murine aspergillosis." Clin Microbiol Infect 2006. 12(4): p. 376-80.
Sheppard et al., "Novel inhalational murine model of invasive pulmonary aspergillosis." Antimicrob Agents Chemother, 2004. 48(5): p. 1908-11.
Sheppard et al., "Standardization of an experimental murine model of invasive pulmonary aspergillosis." Antimicrob Agents Chemother, 2006. 50(10): p. 3501-3.
Spector et al., "Antigen and antibody testing for the diagnosis of blastomycosis in dogs." J Vet Intern Med, 2008. 22(4): p. 839-43.
Staples et al., "Invasive pulmonary aspergillosis in AIDS: radiographic, CT, and pathologic findings" Radiology, 1995. 196(2): p. 409-14.
Steele et al., "The beta-glucan receptor dectin-1 recognizes specific morphologies of Aspergillus fumigatus." PLoS Pathog, 2005. 1(4): p. e42.
Stevens et al., "Interferon-gamma as an antifungal," Journal of Infectious Diseases, vol. 194, Supplement 1, pp. S33-S37 (2006).
Stynen et al., "Rat monoclonal antibodies against Aspergillus galactomannan." Infect Immun, 1992. 60(6): p. 2237-45.
Stynen et al., "A New Sensitive Sandwich Enzyme-Linked Immunosorbent Assay to Detect Galactofuran in patients with Invasive Aspergillosis," J. Clin. Micro., vol. 33, No. 2, Feb. 1995, pp. 497-500.
Suarez et al., "Detection of circulating Aspergillus fumigatus DNA by real-time PCR assay of large serum volumes improves early diagnosis of invasive aspergillosis in high-risk adult patients under hematologic surveillance." J Clin Microbial, 2008. 46(11): p. 3772-7.
Sutherland et al., "In vivo fate and distribution of poly-gamma-D-glutamic acid, the capsular antigen from Bacillus anthracis." Infect Immun, 2008. 76(3): p. 899-906.
Suzuki, E. et al, Clinical and Diagnostic Laboratory Immunology, Sep. 2001, vol. 8(5), pp. 1031-1035, "Reactivity of MEST-1 (Antigalactofuranose) with Trypanosoma cruzi Glycosylinositol Phosphorylceramides (GIPCs): Immunolocalization of GIPCs in Acidic Vesicles of Epimastigotes".
Swanink et al., "Specificity of a sandwich enzyme-linked immunosorbent assay for detecting Aspergillus galactomannan." J Clin Microbial, 1997. 35(1): p. 257-60.
Anastasakou, E et al, ECCMID, 9th, Aspergillus and Aspergillosis Website, Ref. ID 2970, year 1999, abstract, "Detection of antigen galactomannan of Aspergillus in the urine of patients with lung disease."
Ansorg et al., "Aspergillus antigenuria compared to antigenemia in bone marrow transplant recipients." Eur J Clin Microbiol Infect Dis, 1994. 13(7): p. 582-9.

Becker et al., "Galactomannan detection in computerized tomography-based broncho-alveolar lavage fluid and serum in haematological patients at risk for invasive pulmonary aspergillosis." Br J Haematol, 2003. 121(3): p. 448-57.
Bennett et al., "Receptor-mediated clearance of Aspergillus galactomannan." J Infect Dis, 1987. 155(5): p. 1005-10.
Berenguer et al., "Pathogenesis of pulmonary aspergillosis. Granulocytopenia versus cyclosporine and methylprednisolone-induced immunosuppression." Am J Respir Crit Care Med, 1995. 152(3): p. 1079-86.
Boeckh et al., "Plasma polymerase chain reaction for cytomegalovirus DNA after allogeneic marrow transplantation: comparison with polymerase chain reaction using peripheral blood leukocytes, pp65 antigenemia, and viral culture." Transplantation, 1997. 64: p. 108-113.
Brown, Antibodies: key to a robust lateral flow immunoassay, in Lateral Flow Immunoassay, H.Y.T.R.C. Wong, Editor. 2009, Humana Press: New York, N.Y. p. 59-74.
Caillot et al., "Improved management of invasive aspergillosis in neutropenic patients using early thoracic computed tomographic scan and surgery." Journal of Clinical Oncology, 1997. 15(1): p. 139-147.
Clarke, "Urinary antigen diagnosis of meningococcal disease." Br J Biomed Sci, 2000. 57(2): p. 153-5.
Costa et al., "Development of two real-time quantitative TaqMan PCR assays to detect circulating Aspergillus fumigatus DNA in serum," J Microbiol Methods, 2001. 44(3): p. 263-9.
Dupont et al., "Galactomannan antigenemia and antigenemia in aspergillosis: studies in patients and experimentally infected rabbits." J Infect Dis, 1987. 155(1): p. 1-11.
Eskens et al., "Septic shock caused by group G beta-haemolytic streptococci as presenting symptom of acute myeloid leukaemia." Neth J Med, 1995. 46(3): p. 153-5.
Hachem et al., "Utility of galactomannan enzyme immunoassay and (1.3) beta-D-glucan in diagnosis of invasive fungal infections: low sensitivity for Aspergillus fumigatus infection in hematologic malignancy patients." J Clin Microbiol, 2009. 47(1): p. 129-33.
Hines et al., "Pseudomembranous tracheobronchitis caused by Aspergillus." Am Rev Respir Dis, 1991. 143(6): p. 1408-11.
Hoffer et al., "Accuracy of percutaneous lung biopsy for invasive pulmonary aspergillosis." Pediatr Radiol, 2001. 31(3): p. 144-52.
Jensen et al., "Detection of galactomannan and the 18 kDa antigen from Aspergillus fumigatus in serum and urine from cattle with systemic aspergillosis." Zentralbl Veterinarmed [B], 1993. 40(6): p. 397-408.
Kamphuis, HJ (1992) Ph.D. Thesis, Wageningen Agriultural University, pp. 1-157 "Extracellular polysaccharides as target Compounds for the Immunological Detection of Aspergillus and Penicillum in Food" Chapters 1-9, Agricultural University Wageningen, Netherlands.
Khoo et al., "Invasive aspergillosis in patients with AIDS." Clin Infect Dis, 1994. 19 Suppl 1(2): abstract.
Kim et al., "Halo sign on high resolution CT: findings in spectrum of pulmonary diseases with pathologic correlation." J Comput Assist Tomogr, 1999. 23(4): p. 622-6.
Kirsten et al., "Invasive aspergillosis in cavitary lung sarcoidosis." Pneumologie, 1992. 46: abstract.
Latge, Jean-Paul, "Galactofuranose containing molecules in Aspergillus fumigatus" Medical Mycology (2009) vol. 47 (supplement 1), pp. 8104-8109.
Leisenring et al., "A marginal regression modelling framework for evaluating medical diagnostic tests." Statistics in Medicine, 1997. 16(11): p. 1263-1281.
Leitao, E.A. et al, Glycobiology, vol. 13(10), pp. 681-692, 2003, "B-Galactofuranose-containing O-linked oligosaccharides present in cell wall peptidogalactomannan of Aspergillus fumigatus contain immunodominant epitopes."
Levy et al., "The value of bronchoalveolar lavage and bronchial washings in the diagnosis of invasive pulmonary aspergillosis." Respir Med, 1992. 86(3): p. 243-8.
Marr et al., "Antifungal therapy decreases sensitivity of the Platelia Aspergillus galactomannan enzyme immunoassay" Clin Infect Dis. 2005; 40(12):1762-9.

(56) References Cited

OTHER PUBLICATIONS

Marr et al., "Aspergillosis in HSCT recipients: evidence for two distinct pathophysiologic conditions associated with engraftment status." Blood, 2000. 96(11).
Mennink-Kersten et al., "Bifidobacterium lipoteichoic acid and false ELISA reactivity in aspergillus antigen detection." Lancet, 2004. 363(9405): p. 325-7.
Mokkapati et al., "Evaluation of UPlink-RSV: prototype rapid antigen test for detection of respiratory syncytial virus injection." Ann NY Acad Sci, 2007. 1098: p. 476-85.
Nielsen et al., "Prototype single step lateral flow technology for detection of avian influenza virus and chicken antibody to avian influenza virus." J Immunoassay Immunochem, 2007. 28(4): p. 307-18.
Obayashi et al., "Plasma (1→3)-beta-D-glucan measurement in diagnosis of invasive deep mycosis and fungal febrile episodes." Lancet, 1995. 345(8941): p. 17-20.
Ohta, M., et al., "Novel B-D-Galactofuranose-containing High Mannose Type Oligosaccharides in Ascorbate Oxidase from *Acremonium* sp. HI-25", Bioscience, Biotechnology and Biochemistry (1996) vol. 60, No. 7, pp. 1123-1130.
Rath et al., "Value of environmental sampling and molecular typing of aspergilli to assess nosocomial sources of aspergillosis." J Hosp Infect, 1997. 37(1): p. 47-53.
Rogers et al., "Value of antigen detection in predicting invasive pulmonary aspergillosis." Lancet, 1990. 336(8725): p. 1210-1213.
Salonen et al., "Aspergillus antigen in serum, urine and broncholaveolar lavage specimens of neutropenic patients in relation to clinical outcome," Scandinavian Journal of Infectious Diseases, 2000, 32, abstract.
Sarfati, J et al, "Antigens of Aspergillus fumigatus produced in vivo" Journal of Medical and Veterinary Mycology (1995) vol. 33, pp. 9-14.
Slavin et al., "Efficacy and safety of fluconazole prophylaxis for fungal infections after marrow transplantation—a prospective, randomized, double-blind study." Journal Of Infectious Diseases., 1995. 171(6): p. 1545-52.
Tsoni et al., "beta-Glucans and dectin-1." Ann N Y Acad Sci, 2008. 1143: p. 45-60.
Upton et al., "Reproducibility of low galactomannan enzyme immunoassay index values in multiple laboratories." in preparation, 2005.
Van Burik et al., "Panfungal PCR assay for detection of fungal infection in human blood samples." J Clin Microbiol, 1998. 36(5): p. 1169-1175.
Weatherall et al., "Point-of-care urinary pneumococcal antigen less in the emergency department for community acquired pneumonia." Emerg Med J, 2008. 25(3): p. 144-8.
Wiederhold, N. et al., Clinical and Vaccine Immunology, (2009) published online ahead of print Sep. 30, 2009, pp. 1844-1846, vol. 16(12), "Comparison of Lateral Flow Technology and Galactomannan and (1>3)-B-D-Glucan Assays for Detection of Invasive Pulmonary Aspergillus."
Wollschlager et al., "Aspergilloma complicating sarcoidosis. A prospective study of 100 patients." Chest, 1984. 86: p. 585-88.
Furcolow, M. L. 1963. Tests of immunity in histoplasmosis. N. Engl. J. Med. 268:357-361.
Greenspan, Neil, "Defining epitopes: It's not as easy as it seems," Nature Biotechnology 17, 936-937 (1999).
Knutsen et al., "Asp fl CD4+ Th2-like T cell lines in allergic bronchopulmonary aspergillosis." J Allergy Clin Immunol, 1994, 94: p. 215-221.
Whitworth, H. S., M. Scott, D. W. Connell, B. Dongés, and A. Lalvani. 2013. IGRAs—The gateway to T cell based TB diagnosis, Methods 61(1): 52-62.
International Search Report and Written Opinion dated Mar. 18, 2015, from related PCT Patent Application No. PCT/US14/070610.
Non-Final Office Action dated Oct. 20, 2014, in related U.S. Appl. No. 13/511,264.
Response and Amendment filed Nov. 14, 2014, in Response to Office Action dated Oct. 20, 2014, in related U.S. Appl. No. 13/511,264.
Final Office Action dated Jan. 14, 2015, in related U.S. Appl. No. 13/511,264.
Response and Amendment and 1.132 Declarations filed Feb. 10, 2015, in Response to Office Action dated Jan. 14, 2015, in related U.S. Appl. No. 13/511,264.
Non-Final Office Action dated Mar. 24, 2015, in related U.S. Appl. No. 13/511,264.
Response and Amendment and 1.132 Declarations filed May 6, 2015, in Response to Office Action dated Mar. 24, 2015, in related U.S. Appl. No. 13/511,264.
Non-Final Office Action dated Jul. 14, 2015, in related U.S. Appl. No. 13/511,264.
Response and Amendment and 1.132 Declarations filed Jan. 14, 2016, in Response to Office Action dated Jul. 14, 2015, in related U.S. Appl. No. 13/511,264.
Final Office Action dated Mar. 21, 2016, in related U.S. Appl. No. 13/511,264.
Non-Final Office Action dated Apr. 30, 2015, in related U.S. Appl. No. 14/546,830.
Response and Amendment and 1.132 Declarations filed Jun. 11, 2015, in Response to Office Action dated Apr. 30, 2015, in related U.S. Appl. No. 14/546,830.
Final Office Action dated Feb. 23, 2016, in related U.S. Appl. No. 14/546,830.
Response and Amendment filed Apr. 22, 2016, in Response to Office Action dated Feb. 23, 2016, in related U.S. Appl. No. 14/546,830.
Further Response and Amendment filed May 23, 2016, in Response to Office Action dated Feb. 23, 2016, in related U.S. Appl. No. 14/546,830.
Notice of Appeal, Pre-Appeal Brief Request for Review, and Reasons for Review dated Apr. 26, 2016, in Response to Final Office Action dated Mar. 21, 2016, in related U.S. Appl. No. 13/511,264.
Advisory Action dated Feb. 20, 2015, in related U.S. Appl. No. 13/511,264.
USPTO After Final Program Consideration Decision on After Final Consideration Program Request filed Feb. 10, 2015, in related U.S. Appl. No. 13/511,264.
Ampel et al., "Preliminary Evaluation of Whole-Blood Gamma Interferon Release for Clinical Assessment of Cellular Immunity in Patients with Active Coccidioidomycosis," Clinical and Diagnostic Laboratory Immunology, Jun. 2005, p. 700-704.
Ascioglu et al., "Defining opportunistic invasive fungal infections in immunocompromised patients with cancer and hematopoietic stem cell transplants: an international consensus." Clin. Infect Dis, 2002. 34: p. 7-14.
Assi et al. 2013. Histoplasmosis after solid organ transplant. Clin. Infect. Dis. 57(11): 1542-9.
Baddley, J. W., K. L. Winthrop, N. M. Patkar, E. Delzell, T. Beukelman, F. Xie, L. Chen, and J. R. Curtis. 2011. Geographic distribution of endemic fungal infections among older persons, United States. Emerg. Infect. Dis. 17:1664-1669.
Boeckh et al., "Cytomegalovirus pp65 antigenemia-guided early treatment with ganciclovir versus ganciclovir at engraftment after allogeniec marrow transplantation: a randomized double-blind study." Blood, 1996. 88(10): p. 4063-4071.
Boeckh et al., "Effect of high-dose acyclovir on survival in allogeneic marrow transplant recipients who received ganciclovir at engraftment or for cytomegalovirus pp65 antigenemia." J Infect Dis, 1998. 1998(178): p. 1153-7.
Boeckh et al., "Successful modification of a pp65 antigenemia-based early treatment strategy for prevention of cytomegalovirus disease in allogeneic marrow transplant recipients." Blood, 1999. 93(5): p. 1781-2.
Boulware et al., "Rapid diagnosis of pneumococcal pneumonia among HIV-infected adults with urine antigen detection." J Infect, 2007. 55(4): p. 300-9.
Buchheidt et al., "Detection of Aspergillus species in blood and bronchoalvolar lavage samples from immunocompromised patients by means of 2-step polymerase chain reaction: clinical results." Clin Infect Dis, 2001. 33: p. 428-35.

(56) References Cited

OTHER PUBLICATIONS

Cattamanchi, A., R. Smith, K. R. Steingart, J. Z. Metcalfe, A. Date, C. Coleman, B. J. Marston, L. Huang, P. C. Hopewell, and M. Pai. 2011. Interferon-gamma release assays for the diagnosis of latent tuberculosis infection in HIV-infected individuals: a systematic review and meta-analysis. J. Acquir. Immune Defic. Syndr. 56:230-238.

Chaudhary, N., J. F. Staab, and K. A. Marr. 2010. Healthy human T-Cell Responses to Aspergillus fumigatus antigens. PLoS One 5:e9036.

Chothia, C, and A M Lesk. "The Relation between the Divergence of Sequence and Structure in Proteins." The EMBO Journal 5.4 (1986): 823-826.

Chu J. H., C. Feudtner, K. Heydon, T. J. Walsh, and T. E. Zaoutis. 2006. Hospitalizations for endemic mycoses: a population-based national study. Clin. Infect. Dis. 42:822-825.

Clancy et al., "Bronchoalveolar lavage galactomannan in diagnosis of invasive pulmonary aspergillosis among solid-organ transplant recipients." J Clin Microbiol, 2007. 45(6): p. 1759-65.

Costa et al., "Real-Time PCR Coupled with Automated DNA Extraction and Detection of Galactomannan Antigen in Serum by Enzyme-Linked Immunosorbent Assay for Diagnosis of Invasive Aspergillosis." J Clin Microbiol, 2002. 40(6): p. 2224-2227.

Cuenca-Estrella et al., "Value of serial quantification of fungal DNA by a real-time PCR-based technique for early diagnosis of invasive Aspergillosis in patients with febrile neutropenia." J Clin Microbiol, 2009. 47(2): p. 379-84.

Daher, E. F., G. B. Silva, Jr., F. A. Barros, C. F. Takeda, R. M. Mota, M. T. Ferreira, S. A. Oliveira, J. C. Martins, S. M. Araujo, and O. A. Gutierrez-Adrianzen. 2007. Clinical and laboratory features of disseminated histoplasmosis in HIV patients from Brazil. Trop. Med. Int. Health 12:1108-1115.

Dalle et al., "Cryptococcus neoformans Galactoxylomannan contains an epitope(s) that is cross-reactive with Aspergillus Galactomannan." J Clin Microbial, 2005. 43(6): p. 2929-31.

De Sevaux et al., "Microgranulomatous aspergillosis in a patient with chronic granulomatous disease: cure with voriconazole." Clin Infect Dis, 1998. 26(4): p. 996-7.

Deepe, G. S., Jr., and R. Gibbons. 2001. V beta 6+ T cells are obligatory for vaccine-induced immunity to Histoplasma capsulatum. J. Immunol. 167:2219-2226.

Deepe, G. S., Jr., and R. S. Gibbons. 2002. Cellular and molecular regulation of vaccination with heat shock protein 60 from Histoplasma capsulatum. Infect. Immun. 70:3759-3767.

Deepe, G. S., Jr., M. Wuthrich, and B. S. Klein. 2005. Progress in vaccination for histoplasmosis and blastomycosis: coping with cellular immunity. Med. Mycol. 43:381-389. Denning et al., "Efficacy and safety of voriconazole in the treatment of acute invasive aspergillosis." Clin Infect Dis, 2002. 34(5): p. 563-71.

Denning et al., "Efficacy and safety of voriconazole in the treatment of acute invasive aspergillosis." Clin Infect Dis, 2002. 34(5): p. 563-71.

Domenech, J. et al., "Galactomannans from the cell walls of species of Paeci lomyces sect. Paecilomyces and their telemorphs as immunotaxonomic markers" Microbiology, 1999, vol. 145. pp. 2789-2796.

Duong et al., "Kinetic study of host defense and inflammatory response to Aspergillus fumigatus in steroid-induced immunosuppressed mice." J Infect Dis, 1998. 178: p. 1472-82.

Durkin et al., "Diagnosis of coccidioidomycosis with use of the Coccidioides antigen enzyme immunoassay." Clin Infect Dis, 2008. 47(8): p. e69-73.

Einsele et al., "Prediction of invasive pulmonary aspergillosis from colonisation of lower respiratory tract before marrow transplantation." Lancet, 1998. 352(9138): p. 1443.

Ellis et al., "Assessment of the clinical utility of serial beta-D-glucan concentrations in patients with persistent neutropenic fever." J Med Microbiol, 2008. 57(Pt 3): p. 287-95.

Fredricks et al., "Comparison of six DNA extraction methods for recovery of fungal DNA as assessed by quantitative PCR." J Clin Microbial, 2005. 43(10): p. 5122-8.

Gersuk et al., "Dectin-1 and TLRs permit macrophages to distinguish between different Aspergillus fumigatus cellular states." J Immunol, 2006. 176(6): p. 3717-24.

Hage, C. A., and L. J. Wheat. 2010. Diagnosis of pulmonary histoplasmosis using antigen detection in the bronchoalveolar lavage. Expert. Rev. Respir. Med. 4:427-429.

Hansen et al., "Bone marrow transplants from unrelated donors for patients with chronic myeloid leukemia." The New England Journal of Medicine, 1998. 338: p. 962-8.

\* cited by examiner

In the environment, *Histoplasm capsulatum* exists as a mold (1) with aerial hyphae. The hyphae produce macroconidia and microconidia (2) spores that are aerosolized and dispersed. Microconidia are inhaled into the lungs by a susceptible host (3). The warmer temperature inside the host signals a transformation to an oval, budding yeast (4). The yeast are phagocytized by immune cells and transported to regional lymph nodes (5). From there they travel in the blood to other parts of the body (6).

*FIG. 1*

A
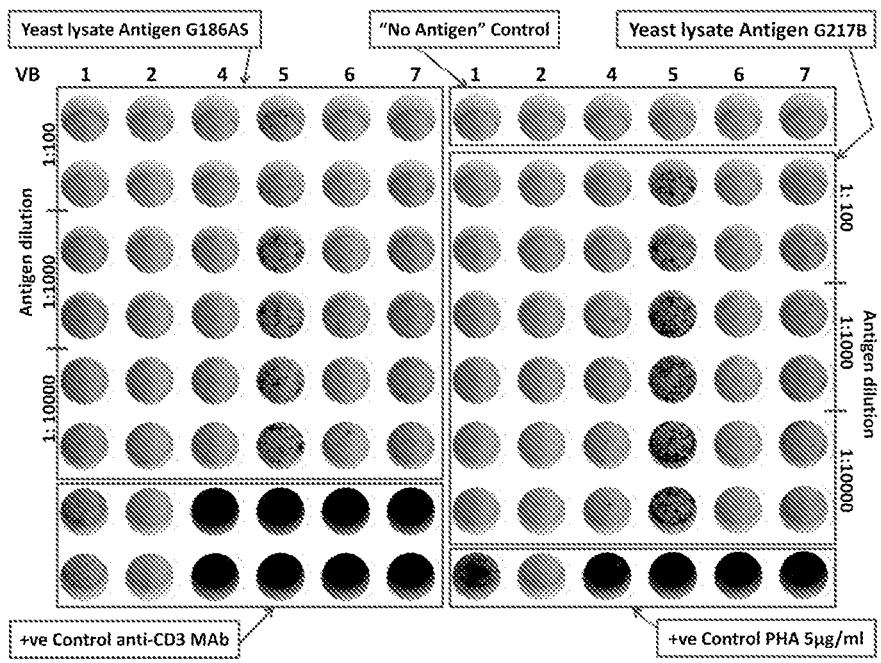
B
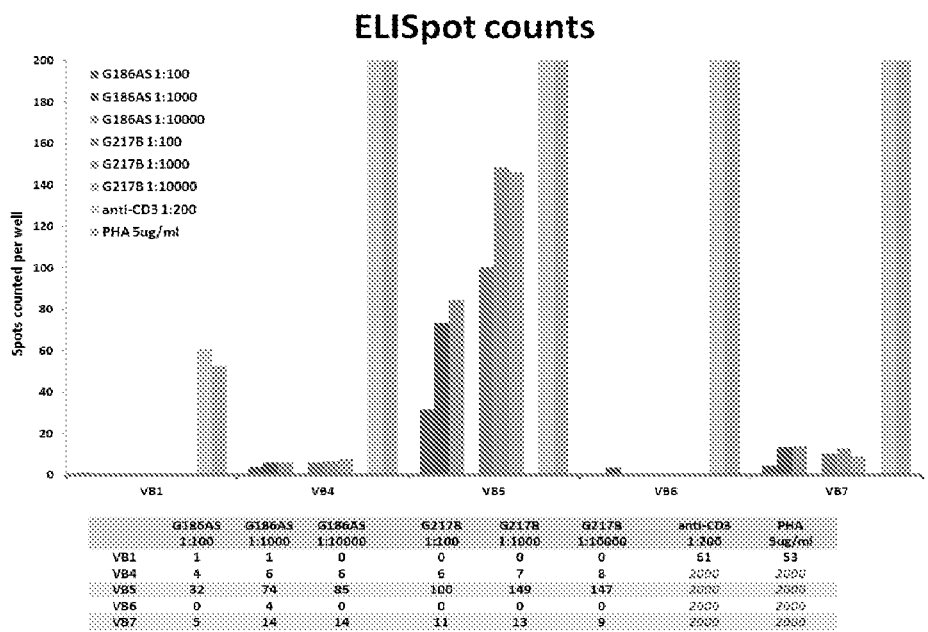
Fig. 3 though a fungus that has a distribution in temperate climates, especially in endemic areas of North, South, and Central America (Scheel et al., 2009; Daher et al., 2007; Huber et al., 2008; Baddley et al., 2011; Chu et al., 2006). Histoplasmosis is the most common endemic mycosis in the U.S. Infection occurs after inhalation exposure to microconidia from mold that grows in soil. After acquisition into the lungs, conidia are ingested by resident and recruited phagocytes, which migrate to resident lymphatic tissue and organs of the reticuloendothelial system (RES). The intracellular yeast form of the organism can remain viable inside macrophages, but robust interferon-gamma (INFγ) Th1 immunity assists to keep disease in check, with development of granulomatous inflammation. Hence, infection is usually asymptomatic or subclinical in subjects who have intact cellular immunity. However, in subjects in whom immunity is impaired, such as subjects with transplanted organs or TNFα inhibition, infection can occur after acquisition and with reactivation of latent infection. Such an infection can be severe or fatal.

INTERFERON-GAMMA RELEASE ASSAYS FOR DIAGNOSIS OF INVASIVE FUNGAL INFECTIONS

CROSS-REFERENCE TO RELATED APPLICATIONS

This application is a 35 U.S.C. § 371 National Stage Entry of International Application No. PCT/US2014/070610 having an international filing date of Dec. 16, 2014, which claims the benefit of U.S. Provisional Application No. 61/916,542, filed Dec. 16, 2013, and U.S. Provisional Application No. 62/062,523, filed Oct. 10, 2014, which are incorporated herein by reference in their entirety.

BACKGROUND

*Histoplasma capsulatum* is a fungus that has a distribution in temperate climates, especially in endemic areas of North, South, and Central America (Scheel et al., 2009; Daher et al., 2007; Huber et al., 2008; Baddley et al., 2011; Chu et al., 2006). Histoplasmosis is the most common endemic mycosis in the U.S. Infection occurs after inhalation exposure to microconidia from mold that grows in soil. After acquisition into the lungs, conidia are ingested by resident and recruited phagocytes, which migrate to resident lymphatic tissue and organs of the reticuloendothelial system (RES). The intracellular yeast form of the organism can remain viable inside macrophages, but robust interferon-gamma (INFγ) Th1 immunity assists to keep disease in check, with development of granulomatous inflammation. Hence, infection is usually asymptomatic or subclinical in subjects who have intact cellular immunity. However, in subjects in whom immunity is impaired, such as subjects with transplanted organs or TNFα inhibition, infection can occur after acquisition and with reactivation of latent infection. Such an infection can be severe or fatal.

Studies performed in the 1960s measured skin-test hypersensitivity to assess exposure (Furcolow, 1963), with results suggesting high rates of latent infection in healthy subjects, with rates some areas exceeding 80%. Establishing the diagnosis of infection and disease, however, remains difficult today. No commercial tests are available to detect skin hypersensitivity responses. Even with active, disseminated disease, diagnosis is difficult, and clinicians are often misled both by the variety of clinical manifestations and the low sensitivity of diagnostic assays. Sensitivity of organism culture and cytopathology is very low; hence, immunodiagnostics have become important.

Reference laboratories currently provide tests to measure circulating antibodies (Ab) and/or antigens (Ag), but the performance of these tests is limited, with low sensitivity of Ab detection, and Ag cross-reactivity with other fungi. With diagnostic limitations, outcomes can be poor. Also, the inability to reliably detect latent infection has limited development of strategies to prevent progression of disease in settings of impending immune suppression, as is done with other latent infections, such as tuberculosis (TB).

The pathogenesis of histoplasmosis and TB are similar. Both infections develop after inhaled exposure of an organism that remains latent in host phagocytes and kept dormant with T-cell dependent host response. Clinical syndromes are almost exactly alike. For years, skin tests to measure delayed type sensitivity to Mycobacterial antigens (Purified Protein Derivative; PPD) were the backbone for identifying prior infection. More recently, T-cell diagnostic assays have revolutionized TB diagnostics, with two commercially available interferon-gamma release assays (IGRAs) now proving to have improved sensitivity and specificity compared to skin testing. Also, these tests allow interpretation of more quantitative Type-1 responses, potentially providing prognostic implications. Being able to uncover latent infection better has enabled therapeutic strategies to prevent TB in subjects with impending immune suppression, such as with organ transplant and TNF-α inhibition. Because of the difficulties of identifying latent infection with pathogenic fungi, therapeutic strategies to prevent active pathogenic fungi infection are not available.

Although infection is typically self-limited in subjects who can mount effective Type-1 responses, severe disease occurs when immune suppressed subjects become acutely infected, and when the host response fails to keep the organism in check, such as with aging, progressive HIV infection, after treatment with biological inhibitors of TNF-α and after transplant (Wood et al., 2003). These are situations in which it would be beneficial to reliably predict latent infection to devise prevention strategies. Instead, now, infection is usually fairly widespread when it is recognized in the subject. A recent retrospective cohort study of documented histoplasmosis in U.S. organ transplant patients noted that most disease was diagnosed after dissemination and associated with a mortality rate of 10% (Assi et al.).

SUMMARY

In one aspect, the presently disclosed subject matter provides a method for diagnosing an invasive fungal infection in a subject, the method comprising: (a) obtaining a biological sample comprising at least one peripheral blood mononuclear cell (PBMC) from a subject; (b) adding at least one antigen from an invasive fungus suspected to be infecting the subject to the biological sample; (c) detecting a T-cell interferon gamma (IFN-γ) response by detecting the IFN-γ produced by the biological sample; (d) comparing the levels of the IFN-γ produced by the biological sample to levels of IFN-γ produced in a control sample that contains no antigen; and wherein a significant difference between the levels of the IFN-γ produced by the biological sample to the levels of IFN-γ produced in the control sample indicates that the subject is infected with the invasive fungus.

In certain aspects, the presently disclosed subject matter provides a diagnostic kit for diagnosing an invasive fungal infection in a subject by detecting an interferon gamma (IFN-γ) response to a fungal antigen, the kit comprising: (a) at least one antigen from a fungus that is suspected of infecting the subject; and (b) at least one reagent for detecting the IFN-γ produced by a biological sample from the subject. In some aspects, the at least one reagent is an antibody that is specific for interferon gamma (IFN-γ). In yet other aspects, the at least one reagent also comprises a secondary detector antibody that can recognize the antibody that is specific for interferon gamma (IFN-γ).

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 2:
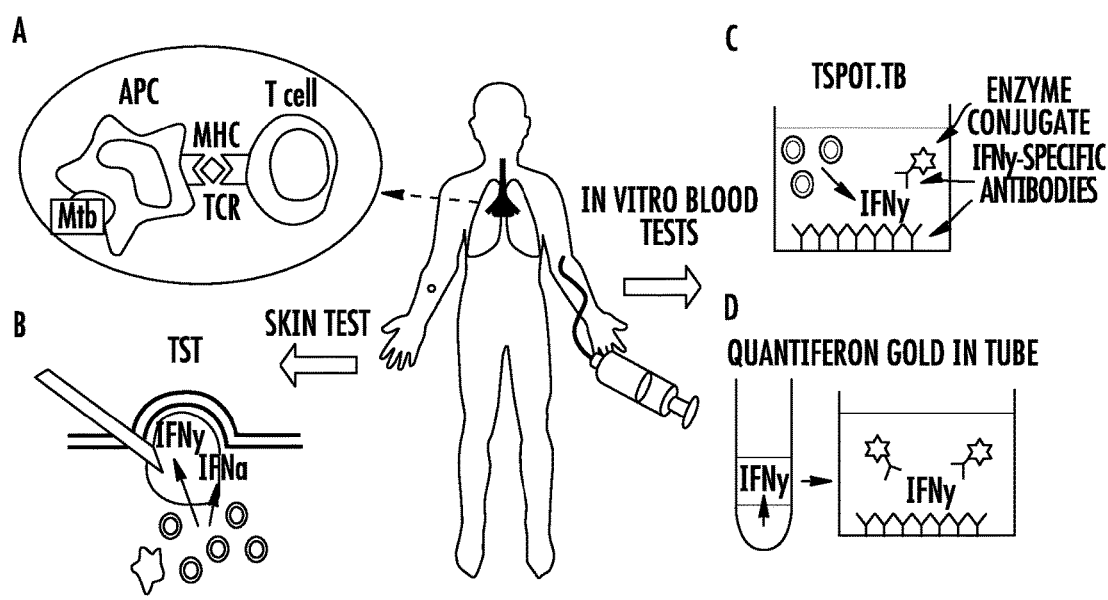

Having thus described the presently disclosed subject matter in general terms, reference will now be made to the accompanying Figures, which are not necessarily drawn to scale, and wherein:

FIG. 1 shows a schematic diagram of the biology of histoplasmosis (from the Centers for Disease Control and Prevention, Atlanta, Ga.);

FIG. 2 shows a schematic diagram of the immunological basis of TST and IGRA, two commercially available IGRAs for TB: (A) upon TB infection, phagocytosis of the mycobacterium in the lung and presentation of antigens by APCs in the hilar lymph node leads to priming of antigen-specific T-cells; (B) the traditionally used TST detects a hypersensitivity reaction in vivo following intradermal injection of TB antigens; and (C, D) IGRAs detect a T-cell IFN-γ response in vitro following overnight stimulation of peripheral blood mononuclear cells (PBMCs) or whole blood with TB Ag (from Whitworth et al, 2013);

FIG. 3 shows an embodiment of a *Histoplasma*-specific ELISPOT assay: (A) ELISPOT plate showing samples utilizing human PBMCs and crude yeast-phase extracts from two *H. capsulatum* isolates (G186AS and G217B); and (B) ELISPOT counts represented as mean antigen-specific spot forming units (SFU);

FIG. 4 shows another embodiment of a *Histoplasma*-specific ELISPOT assay from one subject using two samples separated 2.5 months apart;

FIG. 5 shows another embodiment of a *Histoplasma*-specific ELISPOT assay illustrating repeated positivity to yeast cell lysate (YCL) from different species (indicated), but not to alternative antigen preparations from *H. capsulatum* (e.g. C-antigen, C-Ag) in people with known histoplasmosis and no responses in people without infection: VB9: healthy control, no infection; VB10: healthy control, with latent *histoplasma* infection; VB 11: patient without histoplasmosis; VB12: patient without histoplasmosis who has received non-specific T cell stimulating agent as cancer therapeutic (responses shown are non-specific and can be distinguished from specific responses seen in other infected subjects); VB15: healthy control, with latent histoplasma infection; VB16: patient without histoplasmosis;

FIG. 6 shows the optimization of *H. capsulatum* yeast cell lysate (YCL) concentration for robust response vis-à-vis mitogen (PHA) after 24 hours of incubation (gray bar, 10 μg/mL YCL; striped bar, 50 μg/mL YCL, black bar, 2.5 μg/mL PHA);

FIG. 7 shows optimization of *H. capsulatum* yeast cell lysate (YCL) concentration and optimization of time of incubation of YCL for robust response vis-à-vis mitogen (PHA) after 24 hours and 48 hours of incubation (gray bar, 10 μg/mL YCL; striped bar, 50 μg/mL YCL, black bar, 2.5 μg/mL PHA);

FIG. 8 shows the optimization of input PBMCs for robust response vis-à-vis mitogen (PHA) after 24 hours and 48 hours of incubation (gray bar, 10 μg/mL YCL; striped bar, 50 μg/mL YCL, black bar, 2.5 μg/mL PHA);

FIG. 9 shows the change in YCL and mitogen (PHA) response of PBMC from healthy volunteer VB005 over time;

FIGS. 10A-10D show the frequency distribution of SFU/1e5 cells: (A) in the absence of antigenic stimulus after 24 hours of incubation; (B) in the absence of antigenic stimulus after 48 hours of incubation; (C) using a mitogenic positive control after 24 hours of incubation; and (D) using a mitogenic positive control after 48 hours of incubation; (mitogen 1, PHA; mitogen 2, anti-CD3 MAb);

FIG. 11 shows three representative ELISPOT wells: top well, 10 μg/mL yeast cell lysate (YCL); middle well, 2.5 μg/mL of phytohemagglutinin (PHA); bottom well, no antigen;

FIG. 12 shows the distribution of spot count in ELISPOT-positive and -negative clinical samples after 24 or 48 hours of incubation; and FIG. 13 shows an IFN-γ ELISPOT assay of clinical samples (10 μg/mL yeast cell lysate (YCL) by protein) obtained from people with known latent histoplasmosis ("+") and without ("−").

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Some invasive fungal infections that are problematic to humans include those that are difficult to diagnose. This difficulty is particularly true when fungal antigens are hard to detect and/or culture does not reveal the cause of infection, as with infections that have become chronic, or 'latent' in the host. The presently disclosed subject matter provides methods for diagnosing an invasive fungal infection in a subject by detecting or measuring the release of interferon gamma by the infected subject upon cell exposure to specific microbial antigens. It is believed that the presently disclosed subject matter is the first instance of diagnosing a latent invasive fungal infection in a subject by using cellular specific immunity.

In some embodiments, the presently disclosed methods allow for the diagnosis of an invasive fungal infection by combining a biological sample, such as blood comprising a peripheral blood mononuclear cell (PBMC), from a subject and an antigen from an invasive fungus suspected to be infecting the subject. If the PBMC has previously encountered the antigen, an interferon-gamma (IFN-γ) response will occur, which can be detected by means of an assay. Preferably, the peripheral blood mononuclear cell (PBMC) is a CD3+ T cell, which produces IFN-γ.

As used herein, a "fungus" is a member of a large group of eukaryotic organisms that includes microorganisms such as yeasts and molds. These organisms are classified as a kingdom, fungi, which is separate from plants, animals, protists and bacteria.

As used herein, an "antigen" is a molecule or part of a molecule that can be bound by a major histocompatibility complex (MHC) and presented to a T-cell receptor. Examples of antigens include, but are not limited to, proteins or polypeptides, peptides, polysaccharides, lipids, microbial structures, such as bacterial and fungal cell walls, protozoan cell membranes, bacterial and fungal capsules, viral capsids, viral glycoproteins, microbial toxins, allergens, such as dust mites, pollen, hair, dander, bee venom, drugs, and other agents causing allergic reactions, foreign tissue or cells, and the body's own cells that the body fails to recognize as normal, such as cancer cells, infected cells, and cells involved in autoimmune diseases.

As used herein, the term "infection" refers to the invasion of a host organism's bodily tissues by disease-causing organisms, their multiplication, and the reaction of host tissues to these organisms and the toxins they produce. By "invasive fungal infection," it is meant an infection where fungus has invaded into the deep tissues of a subject and has established itself, resulting in prolonged illness. As used herein, a "latent fungal infection" is a type of fungal infection that lays dormant in a host. Usually a latent infection is an asymptomatic infection capable of manifesting symptoms under particular circumstances or if activated. Many fungal pathogens can remain latent in the body, appearing only when Th1 immunity is depressed because of age, disease, or medical therapies. In general, the presently disclosed subject matter is useful for diagnosing invasive fungal infections, and is particularly useful for diagnosing invasive, latent infections.

The presently disclosed diagnostic methods, kits, and devices are applicable to the detection of invasive fungi. In some embodiments, the fungus is selected from the group consisting of the genus *Histoplasma, Coccidioides, Blastomyces, Paracoccidioides,* and *Cryptococcus*. In other embodiments, the fungus is selected from the group consisting of *Histoplasma capsulatum, Coccidioides immitis, Coccidioides posadasii, Blastomyces dermatitidis, Paracoccidioides brasiliensis, Cryptococcus neoformans,* and *Cryptococcus gattii*. In still other embodiments, the fungus is *Histoplasma capsulatum,* a fungus that infects a subject through the respiratory route and becomes dormant in phagocytic cells that exist in the reticuloendothelial system.

I. Methods for Diagnosing an Invasive Fungal Infection

Accordingly, the presently disclosed subject matter provides a method for diagnosing an invasive fungal infection in a subject, the method comprising: (a) obtaining a biological sample comprising at least one peripheral blood mononuclear cell (PBMC) from a subject; (b) adding at least one antigen from an invasive fungus suspected to be infecting the subject to the biological sample; (c) detecting a T-cell interferon gamma (IFN-γ) response by detecting the IFN-γ produced by the biological sample; (d) comparing the levels of the IFN-γ produced by the biological sample to levels of IFN-γ produced in a control sample that contains no antigen; and wherein a significant difference between the levels of the IFN-γ produced by the biological sample to the levels of IFN-γ produced in the control sample indicates that the subject is infected with the invasive fungus. In some embodiments, at least one peripheral blood mononuclear cell (PBMC) is at least one CD3+ T cell.

As used herein, a PBMC is a blood cell having a round nucleus that is a component of the immune system, such as a lymphocyte, a monocyte, and the like. A T cell or T lymphocyte is a lymphocyte that plays a central role in cell-mediated immunity. Different types of T cells include, but are not limited to, T helper cells, cytotoxic T cells, memory T cells, regulatory T cells (also known as suppressor cells), and natural killer T cells. A T cell can be distinguished from other lymphocytes by the presence of a T cell receptor (TCR) on its cell surface. The CD3 complex is a group of cell surface molecules that associates with the TCR and functions in the cell surface expression of TCR and in the signaling transduction cascade that originates when a peptide: major histocompatibility complex (MHC) ligand binds to the TCR. As used herein, a "CD3+ T cell" is a T cell that is associated with the CD3 complex. In particular embodiments, the biological sample comprises at least one T cell, and in more particular embodiments, the T cell is a CD3+ T cell.

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of an active invasive fungal infection. Moreover, a sample obtained from a patient can be divided and only a portion may be used for diagnosis. Further, the sample, or a portion thereof, can be stored under conditions to maintain sample for later analysis. As used herein, the term "sample" refers to any sampling of cells, tissues, or bodily fluids in which IFN-γ can be detected. In a specific embodiment, a sample comprises a blood sample. In another specific embodiment, the sample comprises peripheral blood mononuclear cells. The definition also includes samples that have been manipulated in any way after their procurement, such as by centrifugation, filtration, precipitation, dialysis, chromatography, treatment with reagents, washed, or enriched for certain cell populations.

A biological sample comprising at least one PBMC can be taken from any part of the subject that comprises at least one PBMC. In a particular embodiment, the biological sample is peripheral blood. By "peripheral blood," it is meant blood that has circulated through the body and comprises platelets, lymphocytes, granulocytes, and erythrocytes. In still other embodiments, at least one PBMC is extracted from peripheral blood after the peripheral blood is taken from the subject by using, for example, a method to separate blood into layers, such as a density gradient. Accordingly, in some embodiments, the methods further comprise fractionating the peripheral blood to obtain at least one peripheral blood mononuclear cell (PBMC), such as by using a Ficoll-Hypaque density gradient. In other embodiments, the biological sample is selected from the group consisting of peripheral blood, fractionated blood and components thereof. In still other embodiments, the biological sample is peripheral blood.

As used herein, the term "control sample," "corresponding control," or "appropriate control" means any control or standard familiar to one of ordinary skill in the art useful for comparison purposes. For example, the control sample may be one that contains no antigen. In another example, the control sample may be one that contains a non-specific mitogen. As used herein, a "mitogen" refers to a chemical substance that encourages a cell to commence cell division, triggering mitosis. A "non-specific mitogen" refers to a mitogen that triggers mitosis selectively in various populations, such as lymphocytes. An example of a non-specific mitogen is phytohemagglutinin (PHA).

"Obtaining" may mean taking a biological sample directly from the subject or patient, or taking a biological sample from the subject indirectly, such as if blood is taken from the subject and then stored, fractionated, or in some other way handled before being used in the presently disclosed methods.

Interferon gamma is a dimerized soluble cytokine that is a member of the type II class of interferons. In humans, the IFN-γ protein (UniProt Accession No. P01579) is encoded by the IFNG gene. In some embodiments, by "T-cell IFN-γ response," it is meant that a CD3+ T-cell responds to an environmental stimulus, such as the presence of an antigen, by producing IFN-γ. A positive T-cell IFN-γ response indicates that the subject has been exposed to, and is at least latently infected with the fungus. A subject that has not had prior exposure to a specific fungus does not have a biological sample that responds to a specific antigen from the fungus by producing IFN-γ.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for treating an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. In some embodiments of the presently disclosed subject matter, the subject is human. In other embodiments, the subject is non-human.

As used herein, the terms "measuring" and "detecting" refer to methods which include detecting the T-cell IFN-γ response to a fungal antigen by detecting the level of IFN-γ or number of IFN-γ producing cells in a sample or subject. In some embodiments, the presently disclosed methods are performed in a reference laboratory.

After obtaining a biological sample from a subject, the biological sample is added to and/or mixed with at least one antigen from an invasive fungus that is suspected of infecting the subject. In some embodiments, at least one antigen from more than one fungus is added in the methods. In other embodiments, multiple different microbial antigens are used in the presently disclosed subject matter. These multiple antigens can be from one species of fungus or from multiple species of fungi. Using more than one species of fungal antigen may be beneficial if it is desirable to eliminate the possibility of more than one type of fungal infection simultaneously or if the therapy for an infected subject will be the same for related fungal infections. It is preferred that the antigens used are immunodominant or recognized significantly by human T-cells after natural infection.

In some embodiments, at least one antigen is added to a biological sample in the form of a fungal extract or lysate. As used herein, an "extract" or "lysate" refers to a solution of cellular proteins resulting when cells are lysed or broken apart, such as by shearing cells. A "crude extract" or "crude lysate" refers to the solution formed when cells are lysed or broken apart with only minimal purification of the cell antigens away from the rest of the cell components. A "partially purified extract" refers to an extract in which antigens have been extracted or purified away from some of the other components of the cell. A "purified antigen" refers to an antigen that has been almost completely or completely separated from the other cell components, including being separated from other types of antigens in the cell extract. Methods for purifying antigens are known in the art, and in the case of protein antigens, include the use of detergents or chaotropic agents to disrupt particles followed by differential extraction and separation of the polypeptides by ion exchange chromatography, affinity chromatography, sedimentation according to density, and gel electrophoresis, for example. Accordingly, in some embodiments, at least one antigen is in a crude fungal extract when it is added to the biological sample. In other embodiments, at least one antigen is in a partially purified fungal extract when it is added to the biological sample.

Antigens used in the presently disclosed subject matter include polypeptides, peptides, polysaccharides, and the like. In some embodiments, at least one antigen comprises at least one protein or fragment thereof, such as the immunogenic part of the protein that is recognized by a T cell. In other embodiments, at least one protein or fragment thereof is at least one purified protein or fragment thereof. In still other embodiments, at least one protein or fragment thereof is at least one recombinant protein or fragment thereof In further embodiments, the antigen is a *Histoplasma*-specific protein recognized by the T-cells of latently infected subjects. Whole genome analysis has documented differential expression of multiple products in both yeast and conidial morphologies, such as CDF1, CBP1, SID4, YPS21, YPS3, SID3, CATB, GAD1, CATA, ALD1, and WHC2. In still further embodiments, at least one protein is selected from the group consisting of CDF1, CBP1, SID4, YPS21, YPS3, SID3, CATB, GAD1, CATA, ALD1, and WHC2. In some embodiments, these proteins can be used as antigens in a standardized assay to test a biological sample for its ability to secrete IFN-γ.

FIG. 1 shows the life cycle of the *Histoplasma capsulatum* organism. In some embodiments, the fungal extract or protein used in the presently disclosed subject matter is from *Histoplasma capsulatum.* In other embodiments, at least one antigen is a yeast-phase antigen from *Histoplasma capsulatum.* The presently disclosed subject matter also includes antigens from other invasive fungi.

After adding at least one antigen to a biological sample, the T-cell IFN-γ response is detected and/or measured. In particular embodiments, the T-cell IFN-γ response is detected by using an immunoassay Immunoassays require biospecific capture reagents, such as antibodies to capture the IFN-γ. In some embodiments, the immunoassay comprises an antibody. Examples of immunoassays include, but are not limited to, enzyme-linked immunosorbent assays (ELISA), enzyme-linked immunosorbent spot (ELISPOT) assays, fluorescence-based immunoassays, immunoblots, Western blots, immunoprecipitation, immunofluorescence, and immunocytochemistry. In addition to antibodies, the presently disclosed subject matter comprises any other suitable agent (e.g., a peptide, an aptamer, or a small organic molecule) that specifically binds to an antigen.

Commonly used immunoassays in diagnostic and research use include radio-immunoassays and enzyme-linked immunosorbent assays (ELISAs). Many of these elaborately configured immunoassays use monoclonal antibodies (MAbs) that possess the ability to bind specifically to the analyte being tested, thereby enhancing the accuracy of the assay. Various approaches have been described for carrying out enzyme immunoassays. A considerable number of these approaches, starting with the earliest of ELISAs, are solid-phase immunoassays in which the analyte to be detected is bound to a solid matrix directly (Direct ELISA) or indirectly (Sandwich ELISA), in which the analyte is captured on a primary reagent. The choice of the solid matrix depends on procedural considerations. A common matrix is the polystyrene surface of multi-well microtiter plates. In some embodiments, the diagnostic device measures secreted IFN-γ levels using an ELISA assay or an ELISPOT assay.

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', F(ab)$_2$, and F(ab')$_2$ fragments. An "antigenic determinant" is the portion of an antigen molecule that determines the specificity of the antigen-antibody reaction. An "epitope" refers to an immunological determinant of an antigen that serves as an antibody-binding site, such as the antigenic determinant of a polypeptide. In some embodiments, when the epitope is an amino acid sequence, an epitope can comprise as few as 3 amino acids in a spatial conformation which is unique to the epitope. Generally an epitope consists of at least 6 such amino acids, and more usually at least 8-10 such amino acids. Many antibodies are available commercially and in addition, antibodies also can be produced by methods well known in the art, e.g., by immunizing animals with the antigens. Antigens can be isolated from samples based on their binding characteristics. Alternatively, if the antigen is a protein and the amino acid sequence is known, the protein can be synthesized and used to generate antibodies by methods well-known in the art.

In the presently disclosed subject matter, the IFN-γ produced by the biological sample is secreted. By "secreted," it is meant that the IFN-γ is transferred from inside the cell to outside the cell. In some embodiments, the IFN-γ is detected by using an enzyme-linked immunosorbent assay (ELISA) or an enzyme-linked immunosorbent spot (ELISPOT) assay.

In some embodiments, the method further comprises comparing the levels of IFN-γ produced by a biological sample to a negative control. In other embodiments, the method further comprises comparing the levels of the IFN-γ produced by the biological sample to levels of IFN-γ produced in a positive control sample. In still other embodiments, a significant difference means at least about a 5-fold difference between the levels of the IFN-γ produced by the biological sample to the levels of IFN-γ produced in the control sample that does not contain any antigen.

As used herein, the term "comparing" refers to making an assessment of how the proportion or level of IFN-γ, or number of IFN-γ producing cells in a fungal antigen-treated sample from a subject relates to the proportion or level of IFN-γ or number of IFN-γ producing cells in a subject's sample that has not been treated with antigen ("control sample"). A significant difference between the sample with antigen and the sample without antigen shows that the subject is infected with the fungus.

As used herein, the terms "significantly different" or "significant difference" mean a level of IFN-γ in a sample that is higher than the level of expression of IFN-γ in a control sample by at least 1.5 fold, 2.0 fold, 3.0 fold, 4.0 fold, 5.0 fold or more. In other embodiments, the terms "significantly different" or "significant difference" mean a level of IFN-γ in a sample that is higher than the level of IFN-γ in a control sample by at least 10 fold, 20 fold, or more.

The presently disclosed subject matter also can be used to diagnose invasive fungal infections that are no longer latent, but are in the active phase. A subject with an active infection caused by a fungus can show symptoms of infection, such as febrile illness, lesions, rash, pneumonia, and the like. In some embodiments, the presently disclosed subject matter can be used to confirm an active fungal infection or can be used to determine the type of fungus that is causing the active infection. Accordingly, in some embodiments, the presently disclosed subject matter includes invasive fungal infections, wherein the invasive fungal infection is active.

In some embodiments, the presently disclosed methods can be used to diagnose, for the prognosis, or the monitoring of a disease state or condition involving an invasive fungal infection. For example, a subject that is going to undergo immunosuppression before a transplant or requires biological inhibitors of immunity can be tested before treatment for latent invasive infections that may reactivate after immunosuppression. If the subject is known to harbor a latent invasive infection, treatment can be given to prevent reactivation of the infection.

As used herein, the term "diagnosis" refers to a predictive process in which the presence, absence, severity or course of treatment of a disease, disorder or other medical condition is assessed. For purposes herein, diagnosis also includes predictive processes for determining the outcome resulting from a treatment. Likewise, the term "diagnosing," refers to the determination of whether a sample specimen exhibits one or more characteristics of a condition or disease. The term "diagnosing" includes establishing the presence or absence of, for example, a target antigen or reagent bound targets, or establishing, or otherwise determining one or more characteristics of a condition or disease, including type, grade, stage, or similar conditions. As used herein, the term "diagnosing" can include distinguishing one form of a disease from another. The term "diagnosing" encompasses the initial diagnosis or detection, prognosis, and monitoring of a condition or disease. The term "prognosis," and derivations thereof, refers to the determination or prediction of the course of a disease or condition. The course of a disease or condition can be determined, for example, based on life expectancy or quality of life. "Prognosis" includes the determination of the time course of a disease or condition, with or without a treatment or treatments. In the instance where treatment(s) are contemplated, the prognosis includes determining the efficacy of a treatment for a disease or condition. The term "monitoring," such as in "monitoring the course of a disease or condition," refers to the ongoing diagnosis of samples obtained from a subject having or suspected of having a disease or condition.

In some embodiments, the presently disclosed subject matter enables detection of reactive circulating T-cells (latent infection) in subjects with mild-moderate immunosuppression, supplementing antigen detection in the setting of disease, and/or enabling development of prevention strategies in subjects with impending biological immunosuppression. Based on the results of the presently disclosed subject matter, further procedures may be indicated, including additional diagnostic tests or therapeutic procedures.

II. Kits for Diagnosing an Invasive Fungal Infection

The presently disclosed subject matter also relates to kits for practicing the methods of the presently disclosed subject matter. In general, a presently disclosed kit contains some or all of the components, reagents, supplies, and the like to practice a method according to the presently disclosed subject matter. In some embodiments, the term "kit" refers to any intended any article of manufacture (e.g., a package or a container) comprising a fungal antigen and a set of particular instructions for practicing the methods of the presently disclosed subject matter.

Accordingly, in some embodiments, the presently disclosed subject matter provides a diagnostic kit for diagnosing an invasive fungal infection in a subject by detecting an interferon gamma (IFN-γ) response to a fungal antigen, the kit comprising: (a) at least one antigen from a fungus suspected to be infecting the subject; and (b) at least one reagent for detecting the IFN-γ produced by a biological sample from the subject. In particular embodiments, the at least one reagent is an antibody that is specific for interferon gamma (IFN-γ). In yet more particular embodiments, the at least one reagent also comprises a secondary detector antibody that can recognize the antibody that is specific for interferon gamma ((IFN-γ). Secondary detector antibodies suitable for use with the presently disclosed methods include, but are not limited to, enzyme labeled antibodies (e.g., peroxidase, alkaline phosphatase (AP), fluorescence labeled antibodies (e.g., FITC, Alexa-Fluor, Qdot), biotin conjugated antibodies, and the like. More generally, in some embodiments, the means for detecting the T-cell IFN-γ response can comprise one or more reagents for performing an immunoassay, such as an ELISA or ELISPOT assay.

In other embodiments, the diagnostic kit further comprises a receptacle for collecting a biological sample from the subject, such as a syringe, tube, a blood collection tube, and the like. In further embodiments, the kit may also include a means for separating at least one PBMC from some of the other blood components, including reagents, columns, and the like.

III. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

*Histoplasma*-Specific ELISPOT Assays

Materials and Methods: The *Histoplasma*-specific ELISPOT assay utilized PBMC harvested from human volunteers with, and without known histoplasmosis, testing reactivity to crude yeast-phase extract from two isolates. Lysates from *H. capsulatum* isolates G186AS and G217B (which lacks α-glucan) were prepared by cell shearing, with protein concentrations measured prior to use using the bicinchoninic acid assay (BCA assay). PBMCs were separated by Ficoll-Hypaque density gradients from multiple subjects, including one patient being treated for documented disseminated histoplasmosis, and other laboratory volunteers. Cells in RPMI media (supplemented with 10% FBS) were enumerated by hemacytometer, mixed with YCL and positive control antigens (phytohemagglutinin, PHA), for indicated time durations and plates (Mabtech) were processed according to manufacturer specifications.

IFN-γ production was measured using a commercially available kit. Briefly, plates were incubated at 37° C. for 24 hrs, washed, and AP-conjugated secondary antibodies to IFN-γ were added. Wells were washed, plates were dried overnight, and spots were visualized and enumerated. Results are represented as mean antigen-specific spot forming units (SFU) after subtraction of background control wells containing no antigen. Results were measured as positive, negative, or indeterminate (lacking a positive control response).

Results: Prior studies had shown that ELISPOT assays could detect fungal antigen-specific T-cells in human blood (Chaudhary et al., 2010). Fungus-specific T-cells (CD4 and CD8) could be successfully detected both by quantifying released IFN-γ and with ELISPOT technology, specifically in the setting in which healthy subjects have developed cellular immune responses to *Aspergillus fumigatus* (Chaudhary et al., 2010). Although fungus-specific T-cells could be detected for a non-latent fungus such as *Aspergillus*, however, diagnosis of latent infection with a pathogenic fungus, such as *Histoplasma*, has been limited.

For the development of a *Histoplasma*-specific ELISPOT assay, PBMC were harvested from human volunteers with and without known histoplasmosis and reactivity to crude yeast-phase extract from two isolates was tested. Representative results are shown visually in FIG. 3. In these data, volunteer blood ("VB") from subjects are listed across the top, after exposure to both yeast lysates (G186AS left, G217B right), diluted as indicated. Positive controls included anti-CD3 MAb and the mitogen, phytohemagglutinin (PHA). The anti-CD3 MAb acts as a positive control by cross-linking the CD3 on a T cell, thereby causing secretion of IFN-γ by the CD3+ T cell. One donor (VB5) responded with a vigorous spot forming units (SFU) response to all dilutions of both yeast antigens. This donor was a healthy infectious diseases physician and lifetime resident of a highly endemic region (Tennessee) who had known granulomatous disease (as seen by chest X-rays) that is representative of latent histoplasmosis. This donor had tested negative for TB exposure with occupational performed TB-Quantiferon assays. Other volunteers (VB2, 4, 6, and 7) had no known granulomatous disease and had not resided in *Histoplasma*-endemic regions. The one volunteer who was being treated for disseminated histoplasmosis (VB1) actually had a weak positive mitogenic response, but not enough CD3+ T-cells to measure a *Histoplasma* specific response.

Figure 4:
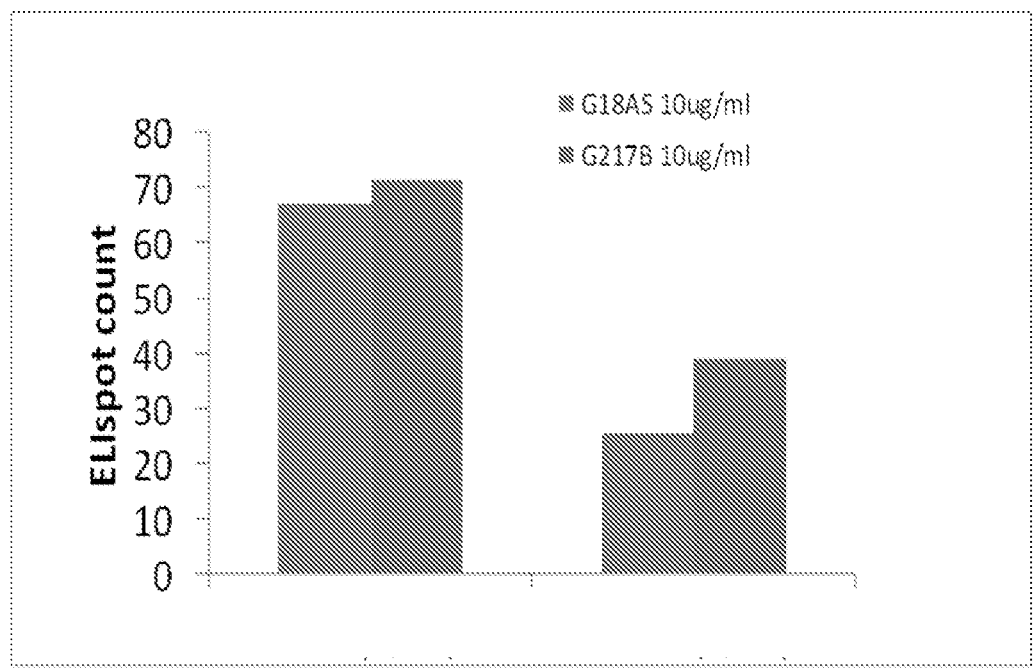
Figure 5:
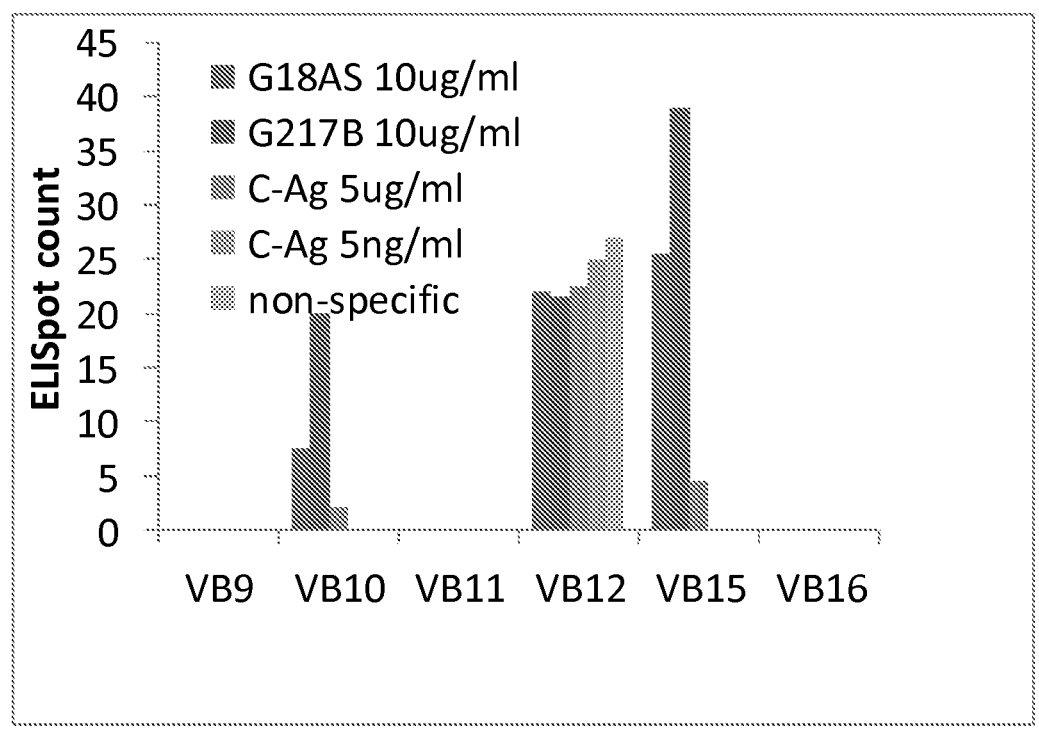
Figure 6:
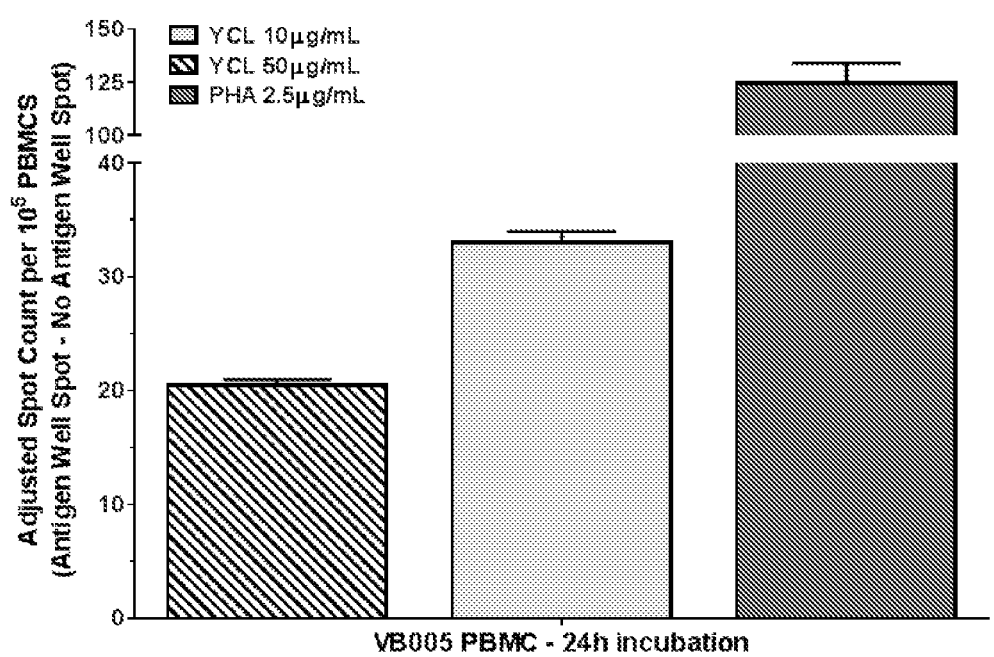
Figure 7:
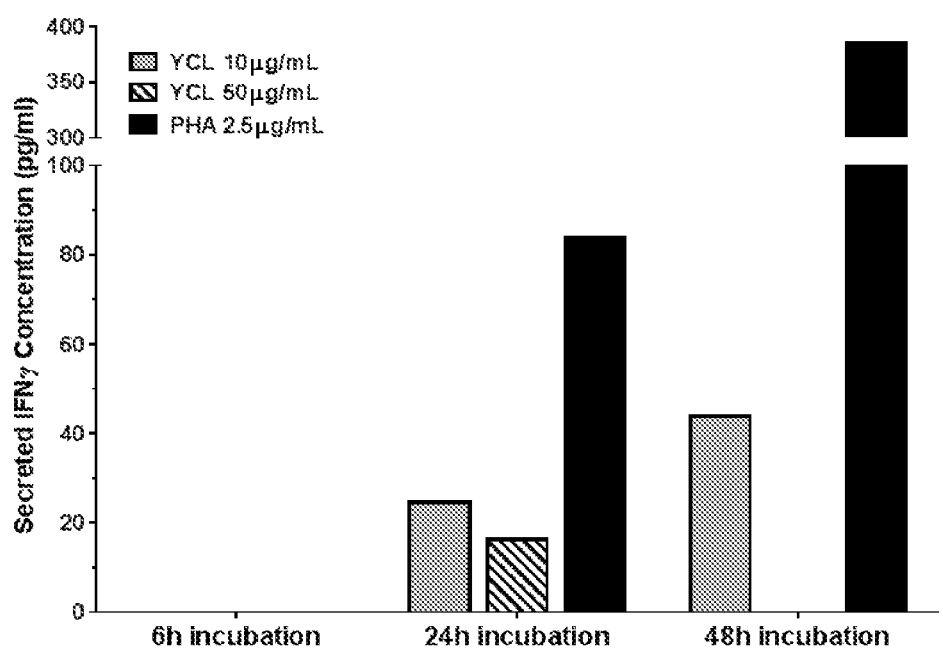
Figure 8:
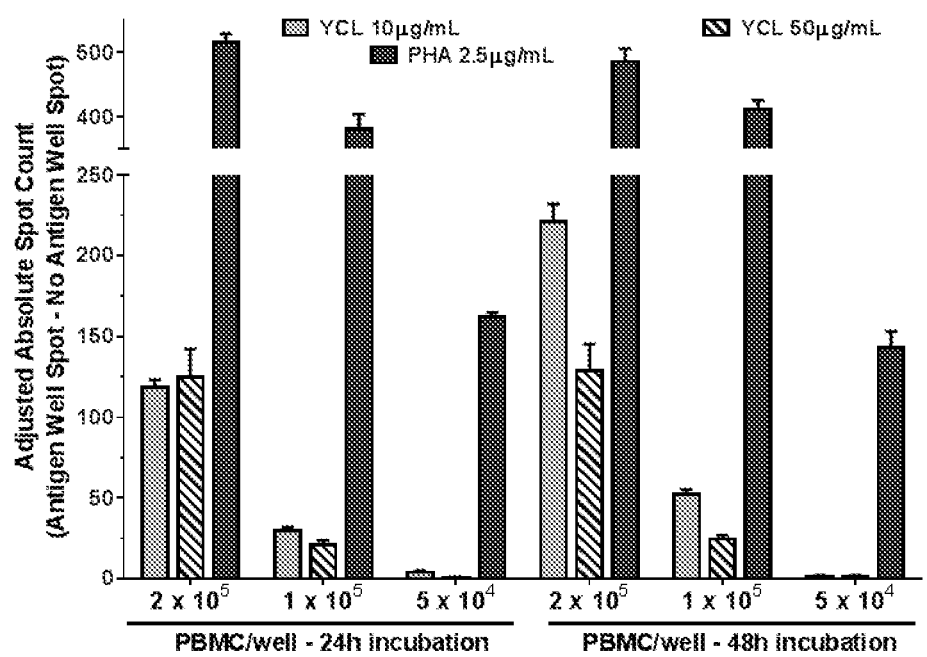
Figure 9:
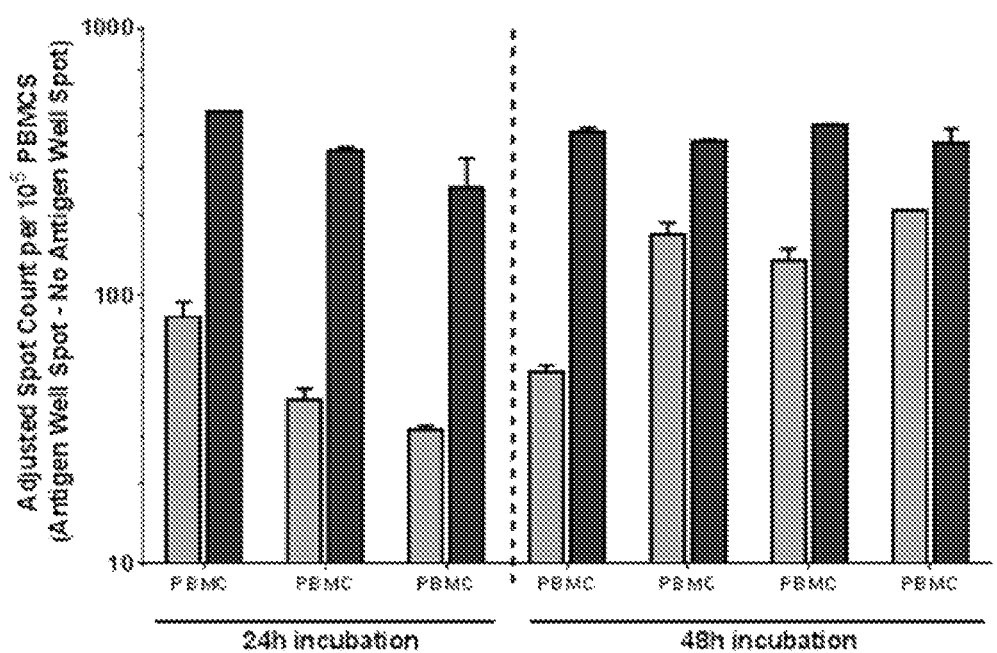
Figure 10:
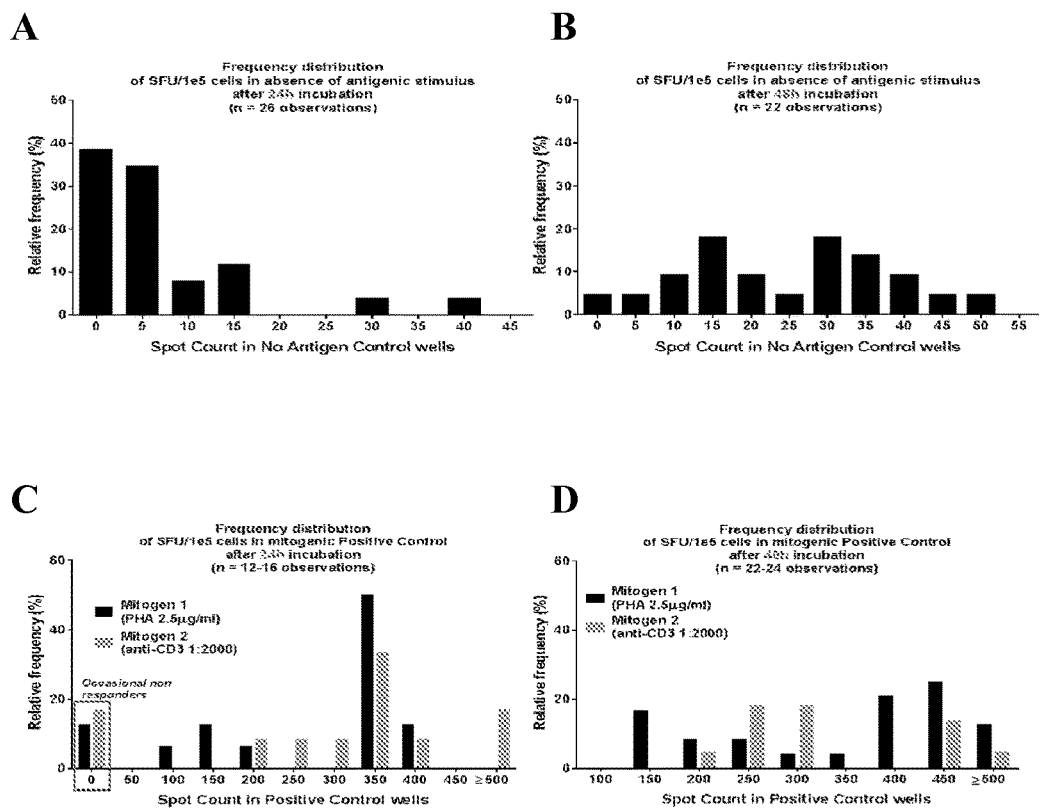
Figure 11:
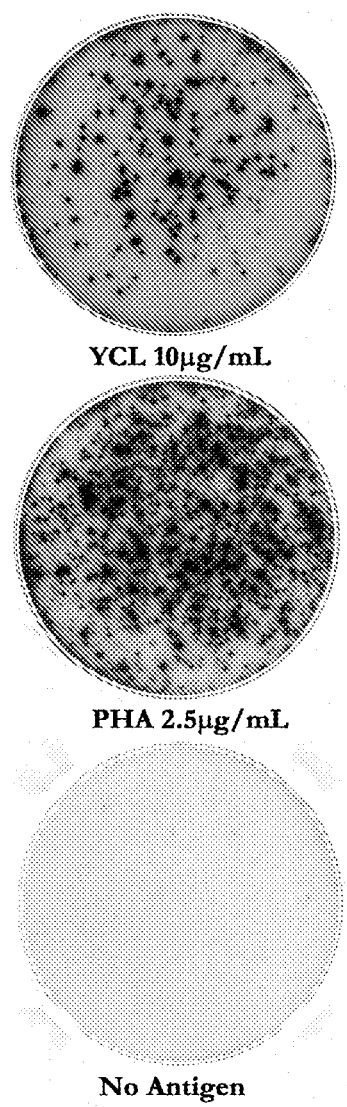
Figure 12:
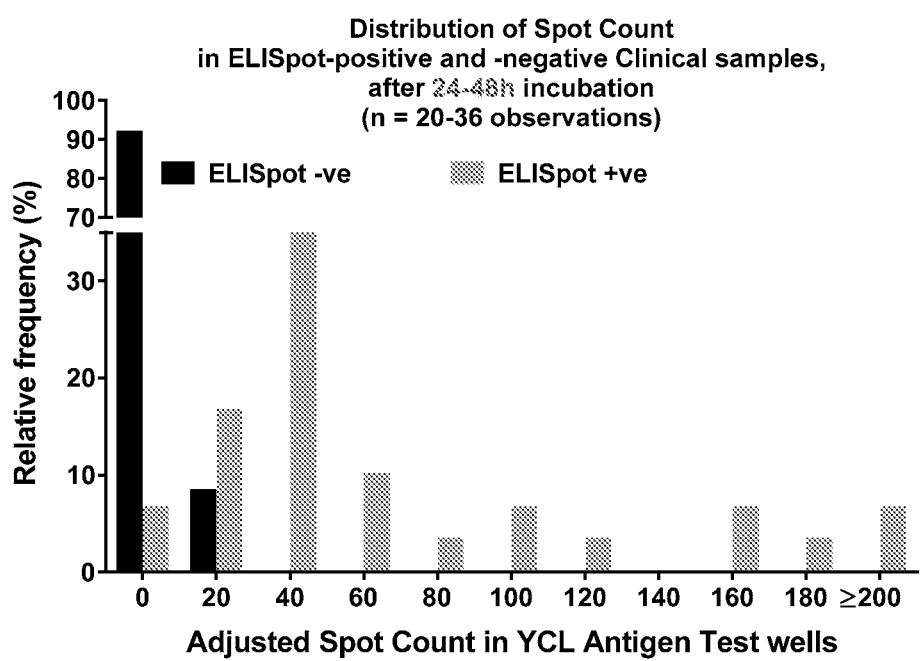
Figure 13:
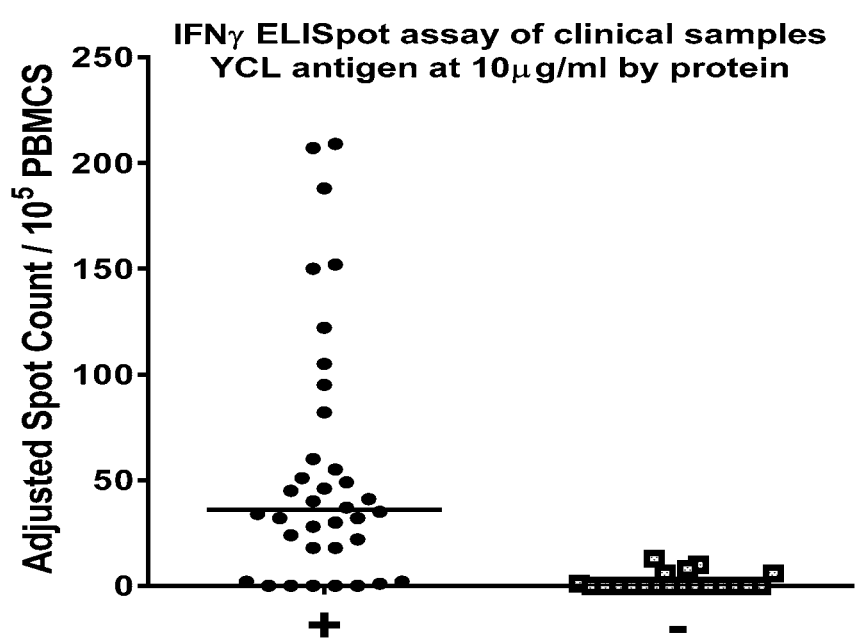

Repeat results using the same methodology show that the positive results from one donor are reproducible although separated by time (FIG. 4). Responses assessed from other volunteers (FIG. 5) show repeated positivity in people with known histoplasmosis (subject VB10 and VB15), and no responses in people without infection (VB9, VB11, VB16) (repeated experiments not shown). This also shows one subject who had non-specific reactivity caused by receipt of a T cell stimulating agent for cancer chemotherapy (VB12).

These results show that a latent fungal infection, such as latent histoplasmosis, is detectable by measurement of reactive CD3+ T-cells after exposure to crude yeast phase antigen. There was remarkably little non-specific reactivity in other healthy volunteers. Without wishing to be bound to any one particular theory, dilution studies did suggest that there was an inhibitory molecule in the crude yeast lysate, but this was less well appreciated in the lysate from the yeast that lacked α-glucan (G217B), which generated more robust responses at all dilutions. These studies demonstrate that T-cells reactive to fungal antigens can be effectively measured in human peripheral blood mononuclear cells, and that this can be used as a diagnostic assay for latent fungal infection.

Example 2

*Histoplasma*-Specific ELISPOT Assay Optimization

Materials and Methods: To perform assay optimization, healthy volunteers from endemic areas and patients with suspected infection were recruited to provide blood. Lysates from *H. capsulatum* isolate G217B were prepared as disclosed in Example 1. Peripheral blood mononuclear cells (PBMCs) were harvested, separated, counted and used in assays to measure IFNγ release after exposure to multiple *Histoplasma* antigen preparations, using ELISA and ELISPOT, with phytohemagglutinin (PHA) as a positive control. Antigen-specific spot-forming units or concentration of IFNγ (pg/mL) were calculated for cells tested. One volunteer with known latent histoplasmosis had a very robust response and was used for optimization and reproducibility studies.

Results: IFNγ release assays were optimized by varying yeast cell lysate (YCL) concentrations, time of incubation, and the number of PBMCs added to the assay. Results showed that the optimal YCL concentration was 10 μg/ml (FIG. 6) and the optimal time of incubation was 48 hours (FIG. 7). The minimum cell input per well was found to be $10^5$ PBMCs (FIG. 8). The signals were enhanced by 48 hour incubation (FIG. 8) and this length of incubation also appeared to stabilize the positive control (mitogen PHA) and YCL responses in serial samples from healthy volunteer VB5 (FIG. 9; serial samples were taken initially and then approximately 2 months and 9 months after the initial assay). FIG. 10 shows the spot count in control wells with no antigen added after 24 hours of incubation (Panel A) and 48 hours of incubation (Panel B), as well as the spot count when positive controls PHA (mitogen 1) or anti-CD3 MAb (mitogen 2) were added and incubated for 24 hours (Panel C) and 48 hours (Panel D). FIG. 11 shows representative ELISPOT wells from a yeast cell lysate sample, positive control PHA, and no antigen. FIG. 12 shows the distribution of spot count in ELISPOT-positive and -negative clinical samples after 24-48 hours of incubation. It was demonstrated that there is a reasonably large variability in spot forming units (SFU) in people who have latent infection, but people who don't have latent infection have relatively few measurable SFU.

The IFNγ release assays were used to screen volunteers (Table 1). Two of the volunteers exhibited robust responses to yeast cell lysate (YCL) from *H. capsulatum* strain G217B, with less response to YCL from a different strain and C-antigen. Assay optimization produced reproducible measurements of approximately 100 spot-forming units/$10^5$ cells with ELISPOT and measureable quantities (25-50 pg/mL) of IFN-γ released by ELISA. Positive responses were reproducible with repeated assay and differential blood draws. Controls with no known exposure or latent disease demonstrated no response to *Histoplasma* YCL.

FIG. 13 shows an IFN-γ ELISPOT assay of all the clinical samples obtained from people with known latent histoplasmosis ("+") and without ("−"). The results show that the presently disclosed methods can be used to diagnose people with latent histoplasmosis.

TABLE 1

Study Subjects

| Subject | Underlying condition | Endemicity | Clinical disease | Clinical diagnosis | ELISPOT YCL ASC[1] | ELISPOT result[2] |
|---|---|---|---|---|---|---|
| VB10 | Healthy | OH | None | Possible latent histoplasmosis | 31 ± 9 | Positive |
| VB16 | Patient | PA | Fatigue, weight loss | Probable "fungal folliculitis", no growth (histopathology) | 28 ± 30 | Positive |
| VB17 | Patient | Ontario | AML, pulmonary nodules | Probable fungal pneumonia (serum GM) | 18 | Positive |
| VB33 | Patient | VA | Disseminated histoplasmosis after kidney transplant | Proven histoplasmosis (Culture, urine Ag) | 35 ± 7 | Positive |
| VB8 | Healthy | OH | None | None | 0 | Negative |
| VB7 | Healthy | MD | None | None | 6 ± 6 | Negative |
| VB6 | Healthy | MD | None | None | 0 | Negative |
| VB4 | Healthy | MD | None | None | 3 ± 4 | Negative |
| VB29 | Patient | PA | Sjogren's, pancytopenia, splenomegaly, pulmonary nodules | Probable histoplasmosis (weak positive urine Ag) | 1 | Negative |
| VB11 | Patient | PA | CLL, pulmonary nodules | Probable aspergillosis (BAL GM) | 0 | Negative |
| VB2 | Patient | El Salvador | ALL s/p hyper-CVAD, | Probable aspergillosis (serum GM) | 0 | Negative |
| VB12 | Patient | DE | AML, pulmonary nodules | Probable aspergillosis (serum GM) | 0 | Negative |
| VB30 | Patient | PA | AdenoCA, Pulmonary cryptococcus | Proven cryptococcosis | 5 | Negative |
|  | Patient | MD | AML, pulmonary nodules, skin lesions | Possible fungal pneumonia (all negative) | 0 | Negative |
| VB1 | Patient | TN | Disseminated histoplasmosis after TNF-α inhibitor | Proven Histoplasmosis (Culture, urine Ag) | 0 | IND[3] |

[1]ASC = Adjusted Spot Count (Antigen Well Spot count − No Antigen Well Spot count) per $10^5$ cells;
[2]Cut-off: 10 spots;
[3]IND = Indeterminate; PHA response <100 spots.

Example 3

Discussion

Lack of sensitive diagnostic tests for histoplasmosis currently delays treatment of symptomatic disease, and limits the ability to prevent disease progression in the setting of latency. Unlike TB, no commercial tests are available to detect skin hypersensitivity; the equivalent of the "histo PPD" does not exist. Even with active disease, diagnosis is difficult, and clinicians are often misled by the variety of clinical manifestations. Even in the setting of active disease, sensitivity of culture is less than 60% (Hage and Wheat, 2010). Similarly, detection of the organism by cytopathology is rare. For these reasons, current standards rely on immunodiagnostics, with detection of circulating antibodies, and/or the presence of cellular antigen in serum or urine. These tests are run by only a couple of reference laboratories in the U.S. and are not available in less developed areas of the world. Performance of assays is variable, and dependent on the population studied. For instance, antibodies are detected only late after infection and are unreliable; the sensitivity of Ab detection in AIDS patients are estimated at only 10% (Hage and Wheat, 2010). In the setting of active disease having high fungal burden, antigen can be detected. Reported sensitivities of antigen assays range between 50-80%, depending on the host, disease, and type of assay (Hage and Wheat, 2010). As this only occurs with late and advanced disease, outcomes of treatment are poor. There is currently no reliable way to devise preventative algorithms in subjects who have high risks for reactivation of latent disease due to impending immune suppression; this is a critical clinical gap given the increasing population of subjects in the U.S. who are exposed to medical therapies that suppress defenses, and aging of the population. As used herein, the term "risk" refers to a predictive process in which the probability of a particular outcome is assessed.

Histoplasmosis develops after microconidia of the organism that grows in the environment are inhaled into the lung (FIG. 1). The organism is ingested by resident and recruited phagocytes, such as macrophages, dendritic cells and neutrophils. Intracellular yeasts can remain viable inside macrophages, where they are transported to local lymph nodes, spleen and organs of the reticuloendothelial system. There, the yeast is kept in check by an interferon gamma dependent Th1 response (Kroetz and Deepe, 2012). A critical feature that supports development of T-cell diagnostics is that, like Mycobacterium tuberculosis, which causes TB, *H. capsulatum* exists in a latent state, with T-cell immunity limiting progressive disease. Measurement of the T-cell response itself thus serves as a very useful adjunctive diagnostic; only subjects with latent disease harbor T-cells reactive to specific antigens. Quantitative results also potentially serve as markers to predict risks for progressive disease. This concept has propelled development of two commercially available IGRAs for TB (FIG. 2), which have essentially revolutionized current diagnostic approaches over the last 10 years. The assays provide enhanced sensitivity and specificity compared to PPDs (Cattamanchi et al., 2011; Whitworth et al., 2013).

The presently disclosed subject matter provides novel technology for diagnosing an invasive fungal infection in a subject by measuring the release of interferon gamma (IFN-γ) by the infected subject upon cell exposure to specific microbial antigens.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Assi et al. 2013. Histoplasmosis after solid organ transplant. *Clin. Infect. Dis.* 57(11): 1542-9.

Baddley, J. W., K. L. Winthrop, N. M. Patkar, E. Delzell, T. Beukelman, F. Xie, L. Chen, and J. R. Curtis. 2011. Geographic distribution of endemic fungal infections among older persons, United States. *Emerg. Infect. Dis.* 17:1664-1669.

Cattamanchi, A., R. Smith, K. R. Steingart, J. Z. Metcalfe, A. Date, C. Coleman, B. J. Marston, L. Huang, P. C. Hopewell, and M. Pai. 2011. Interferon-gamma release assays for the diagnosis of latent tuberculosis infection in HIV-infected individuals: a systematic review and meta-analysis. *J. Acquir. Immune Defic. Syndr.* 56:230-238.

Chaudhary, N., J. F. Staab, and K. A. Marr. 2010. Healthy human T-Cell Responses to *Aspergillus fumigatus* antigens. *PLoS One* 5:e9036.

Chu, J. H., C. Feudtner, K. Heydon, T. J. Walsh, and T. E. Zaoutis. 2006. Hospitalizations for endemic mycoses: a population-based national study. *Clin. Infect. Dis.* 42:822-825.

Daher, E. F., G. B. Silva, Jr., F. A. Barros, C. F. Takeda, R. M. Mota, M. T. Ferreira, S. A. Oliveira, J. C. Martins, S. M. Araujo, and O. A. Gutierrez-Adrianzen. 2007. Clinical and laboratory features of disseminated histoplasmosis in HIV patients from Brazil. *Trop. Med. Int. Health* 12:1108-1115.

Deepe, G. S., Jr., and R. Gibbons. 2001. V beta 6+ T cells are obligatory for vaccine-induced immunity to *Histoplasma capsulatum*. *J. Immunol.* 167:2219-2226.

Deepe, G. S., Jr., and R. S. Gibbons. 2002. Cellular and molecular regulation of vaccination with heat shock protein 60 from *Histoplasma capsulatum*. *Infect. Immun.* 70:3759-3767.

Deepe, G. S., Jr., M. Wuthrich, and B. S. Klein. 2005. Progress in vaccination for histoplasmosis and blastomycosis: coping with cellular immunity. *Med. Mycol.* 43:381-389.

Furcolow, M. L. 1963. Tests of immunity in histoplasmosis. *N. Engl. J. Med.* 268:357-361.

Hage, C. A., and L. J. Wheat. 2010. Diagnosis of pulmonary histoplasmosis using antigen detection in the bronchoalveolar lavage. *Expert. Rev. Respir. Med.* 4:427-429.

Huber, F., M. Nacher, C. Aznar, M. Pierre-Demar, M. El Guedj, T. Vaz, V. Vantilcke, A. Mahamat, C. Magnien, E. Chauvet, B. Carme, and P. Couppie. 2008. AIDS-related *Histoplasma capsulatum* var. *capsulatum* infection: 25 years experience of French Guiana. *Aids* 22:1047-1053.

Inglis, D. O., M. Voorhies, D. R. Hocking Murray, and A. Sil. 2013. Comparative transcriptomics of infectious spores from the fungal pathogen *Histoplasma capsulatum* reveals a core set of transcripts that specify infectious and pathogenic states. *Eukaryot. Cell* 12:828-852.

Kroetz, D. N., and G. S. Deepe. 2012. The role of cytokines and chemokines in *Histoplasma capsulatum* infection. *Cytokine* 58:112-117.

Nosanchuk, J. D., J. N. Steenbergen, L. Shi, G. S. Deepe, Jr., and A. Casadevall. 2003. Antibodies to a cell surface histone-like protein protect against *Histoplasma capsulatum*. *J. Clin. Invest.* 112:1164-1175.

Scheckelhoff, M., and G. S. Deepe, Jr. 2002. The protective immune response to heat shock protein 60 of *Histoplasma capsulatum* is mediated by a subset of V beta 8.1/8.2+ T cells. *J. Immunol.* 169:5818-5826.

Scheel, C. M., B. Samayoa, A. Herrera, M. D. Lindsley, L. Benjamin, Y. Reed, J. Hart, S. Lima, B. E. Rivera, G. Raxcaco, T. Chiller, E. Arathoon, and B. L. Gomez. 2009. Development and evaluation of an enzyme-linked immunosorbent assay to detect *Histoplasma capsulatum* antigenuria in immunocompromised patients. *Clin. Vaccine Immunol.* 16:852-858.

Whitworth, H. S., M. Scott, D. W. Connell, B. Dongés, and A. Lalvani. 2013. IGRAs—The gateway to T cell based TB diagnosis. *Methods* 61(1): 52-62.

Wood, K. L., C. A. Hage, K. S. Knox, M. B. Kleiman, A. Sannuti, R. B. Day, L. J. Wheat, and H. L. Twigg, 3rd. 2003. Histoplasmosis after treatment with anti-tumor necrosis factor-alpha therapy. *Am. J. Respir. Crit. Care Med.* 167:1279-1282.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for diagnosing an invasive fungal infection caused by a fungus from the genus *Histoplasma, Coccidioides, Blastomyces, Paracoccidioides*, or *Cryptococcus* in a subject, the method comprising:
   (a) obtaining a biological sample comprising at least one peripheral blood mononuclear cell (PBMC) from a subject;
   (b) adding at least one antigen from an invasive fungus suspected to be infecting the subject to the biological sample, wherein the invasive fungus is selected from the group consisting of the genus *Histoplasma, Coccidioides, Blastomyces, Paracoccidioides,* and *Cryptococcus;*

(c) detecting a T-cell interferon gamma (IFN-γ) response by detecting the IFN-γ produced by the biological sample;

(d) comparing the levels of the IFN-γ produced by the biological sample to levels of IFN-γ produced in a control sample that contains no antigen; and wherein a significant difference between the levels of the IFN-γ produced by the biological sample to the levels of IFN-γ produced in the control sample indicates that the subject is infected with an invasive fungus selected from the group consisting of the genus *Histoplasma, Coccidioides, Blastomyces, Paracoccidioides,* and *Cryptococcus.*

2. The method of claim 1, wherein the at least one peripheral blood mononuclear cell (PBMC) is at least one CD3+ T cell.

3. The method of claim 1, wherein the invasive fungal infection is latent.

4. The method of claim 1, wherein the invasive fungal infection is active.

5. The method of claim 1, wherein the biological sample is selected from the group consisting of peripheral blood, fractionated blood and components thereof.

6. The method of claim 5, wherein the biological sample is peripheral blood.

7. The method of claim 6, further comprising fractionating the peripheral blood to obtain at least one peripheral blood mononuclear cell (PBMC).

8. The method of claim 1, wherein the at least one antigen is in a crude fungal extract when it is added to the biological sample.

9. The method of claim 1, wherein the at least one antigen is in a partially purified fungal extract when it is added to the biological sample.

10. The method of claim 1, wherein the T-cell IFN-γ response is detected by using an immunoassay.

11. The method of claim 10, wherein the IFN-γ is detected by using an enzyme-linked immunosorbent spot (ELISPOT) assay.

12. The method of claim 10, wherein the IFN-γ is detected by using an enzyme-linked immunosorbent assay (ELISA).

13. The method of claim 1, wherein the fungus is selected from the group consisting of *Histoplasma capsulatum, Coccidioides immitis, Coccidioides posadasii, Blastomyces dermatitidis, Paracoccidioides brasiliensis, Cryptococcus neoformans,* and *Cryptococcus gattii.*

14. The method of claim 13, wherein the fungus is *Histoplasma capsulatum.*

15. The method of claim 14, wherein the at least one antigen is a yeast-phase antigen.

16. The method of claim 1, wherein the at least one antigen comprises at least one protein or fragment thereof.

17. The method of claim 16, wherein the at least one protein or fragment thereof is at least one purified protein or fragment thereof.

18. The method of claim 16, wherein the at least one protein or fragment thereof is at least one recombinant protein or fragment thereof.

19. The method of claim 16, wherein the at least one protein or fragment thereof is selected from the group consisting of CDF1, CBP1, SID4, YPS21, YPS3, SID3, CATB, GAD1, CATA, ALD1, and WHC2.

20. The method of claim 1, wherein a significant difference means at least about a 5-fold difference between the levels of the IFN-γ produced by the biological sample to the levels of IFN-γ produced in the control sample.

21. The method of claim 1, wherein the subject is human.

22. The method of claim 1, wherein the subject is non-human.

23. The method of claim 1, further comprising comparing the levels of the IFN-γ produced by the biological sample to levels of IFN-γ produced in a positive control sample.

* * * * *